US010525282B2

(12) United States Patent
Fairbanks et al.

(10) Patent No.: US 10,525,282 B2
(45) Date of Patent: Jan. 7, 2020

(54) BRACHYTHERAPY RING APPLICATOR DEVICE AND METHOD OF USE THEREOF

(71) Applicant: Kobold, LLC, Liberty Lake, WA (US)

(72) Inventors: Robert K. Fairbanks, Liberty Lake, WA (US); Spencer J. Fillmore, Liberty Lake, WA (US); Wayne T. Lamoreaux, Liberty Lake, WA (US); Christopher M. Lee, Liberty Lake, WA (US)

(73) Assignee: Kobold, LLC, Liberty Lake, WA (US)

( * ) Notice: Subject to any disclaimer, the term of this patent is extended or adjusted under 35 U.S.C. 154(b) by 424 days.

(21) Appl. No.: 15/295,672

(22) Filed: Oct. 17, 2016

(65) Prior Publication Data

US 2017/0106207 A1    Apr. 20, 2017

Related U.S. Application Data

(60) Provisional application No. 62/242,297, filed on Oct. 15, 2015.

(51) Int. Cl.
*A61N 5/10* (2006.01)
(52) U.S. Cl.
CPC ......... *A61N 5/1001* (2013.01); *A61N 5/1016* (2013.01)
(58) Field of Classification Search
CPC ..... A61M 2025/028; A61N 2005/1018; A61N 5/1001; A61N 5/1007; A61N 5/1016; A61N 5/1014
See application file for complete search history.

(56) References Cited

U.S. PATENT DOCUMENTS

| 4,292,960 A | 10/1981 | Paglione |
| 4,331,131 A | 5/1982 | Kumar |
| 5,012,357 A | 4/1991 | Schoeppel et al. |
| 5,562,594 A | 10/1996 | Weeks |
| 6,699,171 B2 | 3/2004 | Harmon |

(Continued)

FOREIGN PATENT DOCUMENTS

| FR | 2401669 A1 | 3/1979 |
| WO | 2007149578 A2 | 12/2007 |

(Continued)

OTHER PUBLICATIONS

"Ring & Tandem Combination Applicator Set", BrachyTherapy Applicators and Accessories, Varian medical systems, Inc, 2011, 10 Pages.

(Continued)

*Primary Examiner* — Kaylee R Wilson
(74) *Attorney, Agent, or Firm* — Workman Nydegger

(57) ABSTRACT

A brachytherapy ring applicator, kit, and method of use is provided. The brachytherapy ring applicatory includes a tandem, ring colpostat, and a bracket assembly. The tandem has a connector on a proximal end of the tandem and a treatment end on a distal end. The ring colpostat includes a ring member on a distal end of the ring colpostat. The bracket assembly is configured to be locked to both a shaft of the tandem and to a shaft of the ring colpostat such that the distal end of the tandem is firmly maintained in a fixed position relative to the distal end of the ring colpostat, and each of the tandem and the colpostat are entirely self-supporting from the bracket assembly to their distal ends.

19 Claims, 19 Drawing Sheets

(56) References Cited

U.S. PATENT DOCUMENTS

| | | | |
|---|---|---|---|
| 7,666,130 | B2 | 2/2010 | Mick |
| 8,033,979 | B2 | 10/2011 | Mick |
| 2002/0032449 | A1 | 3/2002 | Rota et al. |
| 2003/0153803 | A1 | 8/2003 | Harmon |
| 2008/0064916 | A1 | 3/2008 | Mick |
| 2010/0152520 | A1 | 6/2010 | Mick |
| 2012/0123188 | A1 | 5/2012 | Rahimian |
| 2012/0277518 | A1 | 11/2012 | Mick et al. |
| 2013/0006097 | A1 | 1/2013 | Mick et al. |
| 2013/0030238 | A1* | 1/2013 | Kelley ............... A61N 5/1016 600/6 |
| 2013/0109908 | A1* | 5/2013 | Rahimian ............ A61N 5/1016 600/6 |
| 2014/0121444 | A1 | 5/2014 | Van Erp et al. |
| 2015/0065784 | A1 | 3/2015 | Fillmore et al. |

FOREIGN PATENT DOCUMENTS

| | | |
|---|---|---|
| WO | 2011011731 A2 | 1/2011 |
| WO | 2012149417 A1 | 11/2012 |
| WO | 2013177249 A1 | 11/2013 |
| WO | 2014036337 A2 | 3/2014 |
| WO | 2016073596 A1 | 5/2016 |

OTHER PUBLICATIONS

European Search Report from corresponding European Application No. 13832673.1, dated Jul. 5, 2016.

"Varian BrachyTherapy Applicators and Accessories;" Varian Medical Systems, Inc.,www.varian.com/brachytherapy; 2011, 147 Pages.

"HDR CT Compatible Henshke Type Gyn Applicator Gamma-med/ Vari-Source with Click Fit Connector (w/Unshielded Ovoids)," Mick Radio-Nuclear Instruments, Inc., Catalog #0508, Apr. 13, 2009.

"Intracavitary HDR Brachytherapy CT Compatible Henschke T&O Applicator," Mick Radio-Nuclear Instruments, Inc., The Brachytherapy Company; www.micknuclear.com; 2003.

"HDR CT Compatible Henshke Type Gyn Applicator Gamma-med/ Vari-Source with Click Fit Connector (w/Unshielded Ovoids)," Mick Radio-Nuclear Instruments, Inc., Catalog #0508,May 18, 2011.

"Modified Henschke Type Cervix Applicator Kit" Mick Radio-Nuclear Instruments, Inc., Catalog #6402-93M, May 27, 2010.

"HDR CT Compatible Fletcher-Suit-Delclos (FSD) Applicator (with Unshielded Ovoids & without interface Connectors) for Nucletron HDR," Catalog #0819, Instruction Manual, Mick Radio-Nuclear Instruments, Inc., Dec. 16, 2009.

"HDR CT Compatible Fletcher-Suit-Delclos (FSD) Applicator (with Unshielded Ovoids) for GammaMed/Vari-Source HDR," Catalog #0612, Instruction Manual, Mick Radio-Nuclear Instruments, Inc., Mar. 11, 2010.

"HDR CT Compatible Fletcher-Suit-Delclos (FSD) Applicator (with Unshielded Ovoids) for MulitSource HDR" Catalog #0817, Instruction Manual, Mick Radio-Nuclear Instruments, Inc., Dec. 16, 2009.

International Search Report and Written Opinion of corresponding of PCT Application No. PCT/US2013/057413 dated Feb. 7, 2014.

"Intracavitary HDR Brachytherapy CT Compatible FSD T&O Applicator," Mick Radio-Nuclear Instruments, Inc., The Brachytherapy Company; www.micknuclear.com; 2003.

International Search Report from PCT Application No. PCT/US2016/ 057359, dated Feb. 3, 2017.

* cited by examiner

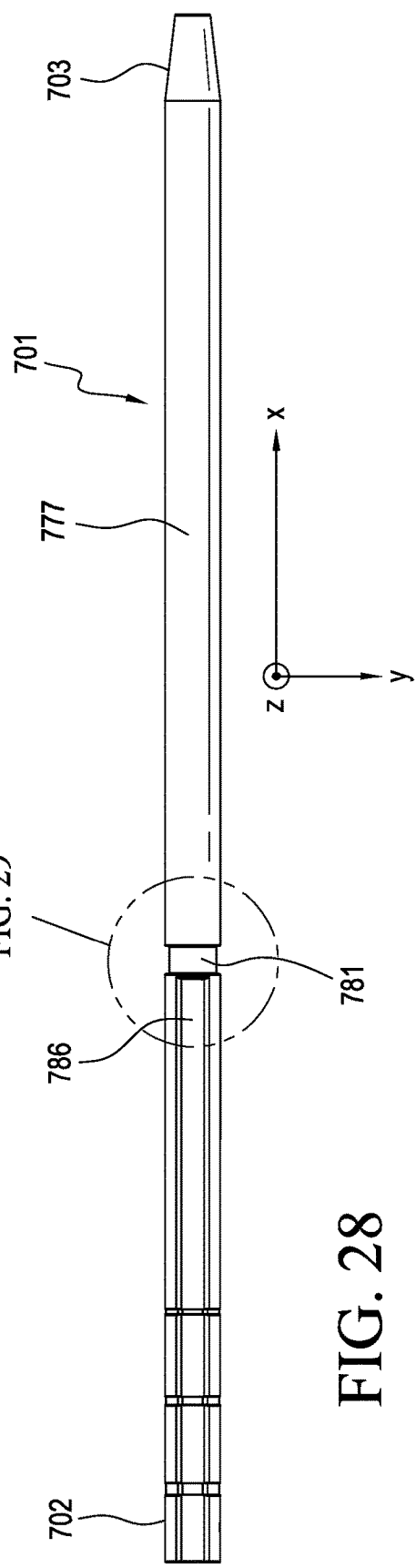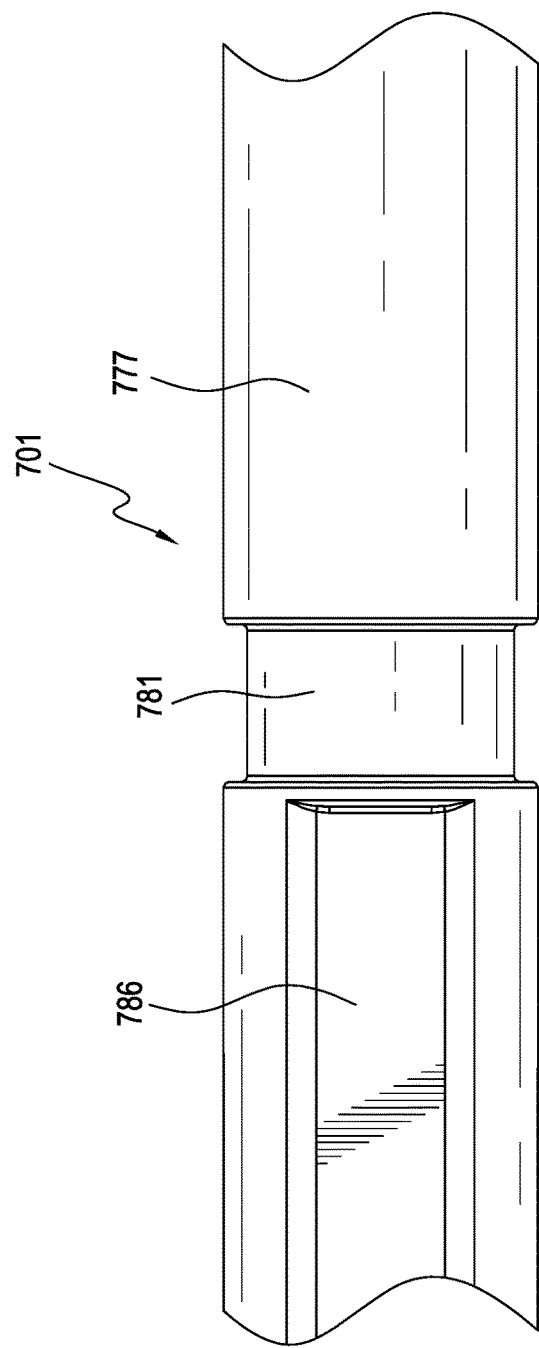

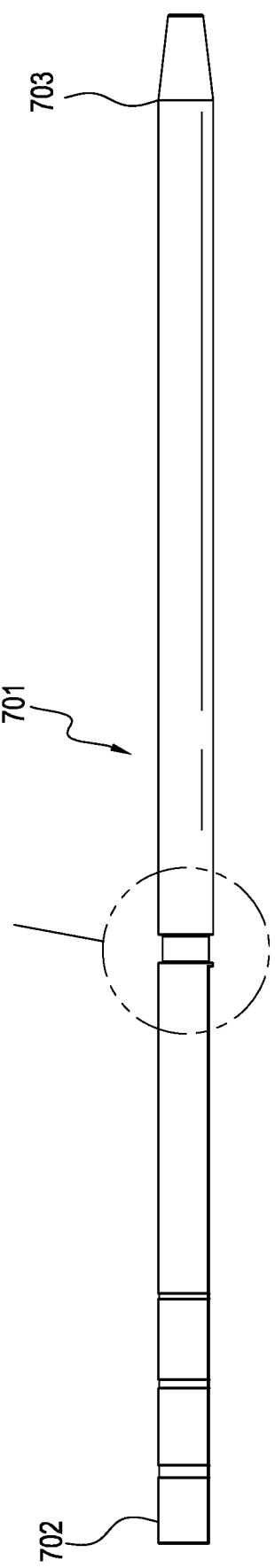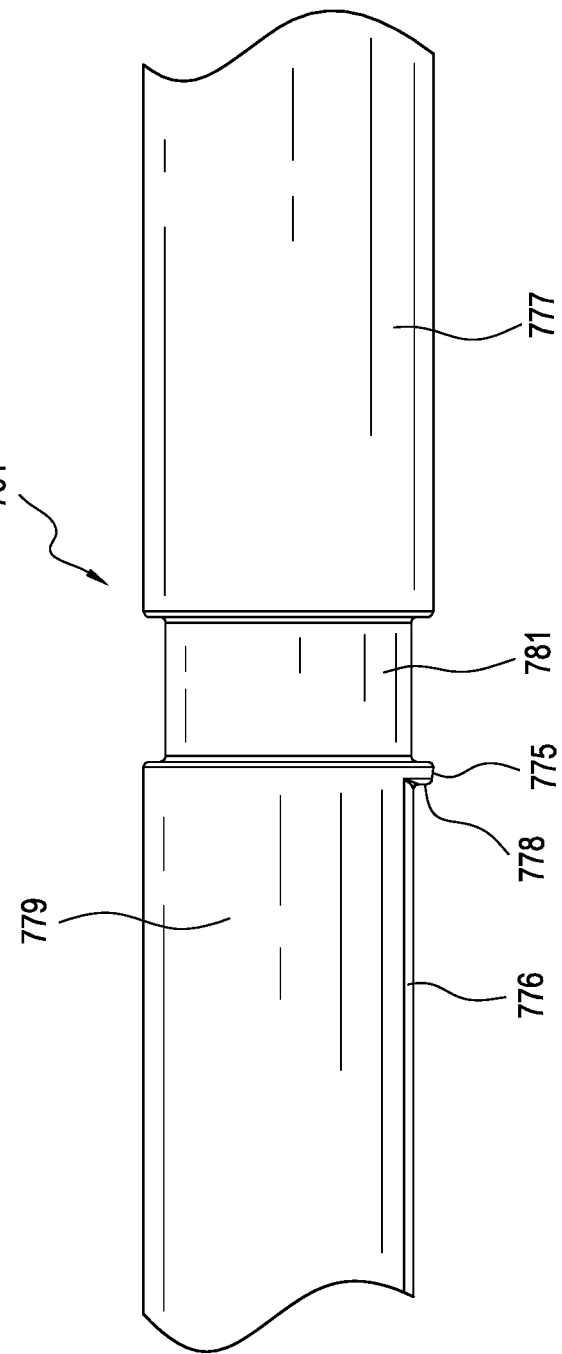

BRACHYTHERAPY RING APPLICATOR DEVICE AND METHOD OF USE THEREOF

BACKGROUND

Technical Field

The present disclosure relates generally to an applicator device for use in delivering radiation therapy, and more particularly to a brachytherapy ring applicator device for use in supplying a radiation source to an internal tumor.

Description of the Related Art

Brachytherapy may be a form of cancer treatment in which radiation sources may be placed inside a patient's body to irradiate an internal tumor. Thus, in brachytherapy, a radioactive source may be placed in or around a tumor. Brachytherapy may have the advantage of delivering high doses of ionizing radiation to small volumes of tissue, combined with a rapid fall off of dose such that distant tissue may be spared. It may have provided excellent results for localized control of various cancers, including, for example, cancer of the vagina, cervix, or uterus.

Afterloading may be a commonly used radiation delivery technique wherein a non-radioactive applicator may be first positioned in the treatment site and then the applicator may be loaded with a radiation source. Once the applicator may be correctly positioned in the patient the applicator may be connected to an afterloading apparatus or machine, which contains the radioactive source, and the radioactive source may be provided to the applicator through a series of connecting guide tubes. The radioactive source remains in place for a specified length of time and then may be drawn back through the tubes to the afterloading apparatus or machine. The applicator may be then removed from the treatment site.

Careful placement of the applicator, and thus, placement of the radioactive source may be important to allow for localized and precise irradiation of the tumor. Additionally, ease of placement and positioning of the applicator may be significant to improve the comfort of the patient and treatment provider during brachytherapy treatment.

SUMMARY

A brachytherapy ring applicator is provided. According to an embodiment, the brachytherapy ring applicator includes a tandem, a ring colpostat, and a bracket assembly. The tandem has a connector end on a proximal end of the tandem and a treatment end on a distal end of the tandem. The treatment end is configured to be arranged in proximity to the area to be treated by a radioactive source. The ring colpostat includes a ring member on a distal end of the ring colpostat. The ring member being configured to position the treatment end of the tandem. The bracket assembly is configured to be locked to both a shaft of the tandem and to a shaft of the ring colpostat such that the distal end of the tandem is firmly maintained in a fixed position relative to the distal end of the ring colpostat. The tandem, the colpostat, and the bracket assembly are configured such that, when the tandem and the ring colpostat are locked to the bracket assembly, tandem, from a location of attachment of the shaft of the tandem to the bracket assembly to the distal end of the tandem, and the colpostat, from the location of attachment of the shaft of the colpostat to the bracket assembly to the distal end of the colpostat, are entirely self-supporting.

A brachytherapy ring applicatory kit is also provided. The brachytherapy ring applicatory kit includes a plurality of tandems, a plurality of ring colpostats, and a bracket assembly. Each of the tandems having a connector end on a proximal end of the tandem and a treatment end on a distal end of the tandem, the treatment end being configured to be arranged in proximity to the area to be treated by a radioactive source. Each of the ring colpostats including a ring member on a distal end of the ring colpostat, the ring member being configured to position the treatment end of the tandem. The bracket assembly is configured to be locked both to both a shaft of one of said plurality of tandems and to a shaft of one of said ring colpostats such that the distal end of said one of said tandems is firmly maintained in a fixed position relative to the distal end of said one of said ring colpostats. The tandems, colpostats, and bracket assembly of the kit are configured such that when one of said tandems and one of said ring colpostats are locked to the bracket assembly, said one of said tandems, from a location of attachment of the shaft of said tandem to the bracket assembly to the distal end of said tandem, and said one of said colpostats, from the location of attachment of the shaft of said colpostat to the bracket assembly to the distal end of said colpostat, are entirely self-supporting.

A brachytherapy method for treating cancer is provided. The method includes the follow steps. A shaft of a ring colpostat is locked to a bracket assembly, the ring colpostat including a ring member on a distal end of the ring colpostat, the ring colpostat being separable from the bracket assembly. A tandem is inserted into a patient, the tandem having a connector end on a proximal end of the tandem and a treatment end on a distal end of the tandem, the treatment end being configured to be arranged in proximity to the area to be treated by a radioactive source. The ring member of the ring colpostat is passed around the connector end of the tandem and passing the ring member along a shaft of the tandem to provide the ring member within proximity to the treatment end of the tandem and the proximity to the area to be treated. A shaft of the tandem is locked to the bracket assembly, the tandem being separable from the bracket assembly. The bracket assembly is configured to be locked to both the shaft of the tandem and to the shaft of the ring colpostat such that the distal end of the tandem is firmly maintained in a fixed position relative to the distal end of the ring colpostat. The tandem, the colpostat, and the bracket assembly are configured such that, when the tandem and the ring colpostat are locked to the bracket assembly, the tandem, from a location of attachment of the shaft of the tandem to the bracket assembly to the distal end of the tandem, and the colpostat, from the location of attachment of the shaft of the colpostat to the bracket assembly to the distal end of the colpostat, are entirely self-supporting.

A brachytherapy ring applicator device is provided. In one example, a brachytherapy ring applicator may include a tandem, a ring colpostat, and a bracket assembly. The tandem may have a connector end on a proximal end of the tandem and a treatment end on a distal end of the tandem. The treatment end may be configured to be arranged in proximity to the area to be treated by a radioactive source. The ring colpostat may include a ring member on a distal end of the ring colpostat. The bracket assembly may be configured to be locked to a shaft of the tandem and to a shaft of the ring colpostat in such a way that the distal end of the tandem remains in a fixed position relative to the distal end of the ring colpostat. The bracket assembly may be detachably separable from the tandem and from the ring colpostat. The brachytherapy ring applicator may be configured such that all portions of the bracket assembly may be maintained outside a patient during treatment and no support mechanism may be provided between the bracket assembly and the distal end of the tandem or the distal end of the ring colpostat.

A brachytherapy method for treating cancer is also provided. According to one example, a shaft of a ring colpostat may be locked to a bracket assembly, the ring colpostat including a ring member on a distal end of the ring colpostat and the ring colpostat being separable from the bracket assembly. A tandem may be inserted into a patient, the tandem having a connector end on a proximal end of the tandem and a treatment end on a distal end of the tandem, the treatment end being configured to be arranged in proximity to the area to be treated by a radioactive source. The ring member of the ring colpostat may be passed around the connector end of the tandem and the ring member may be passed along a shaft of the tandem to provide the ring member within proximity to the treatment end of the tandem and the proximity to the area to be treated. A shaft of the tandem may be locked to the bracket assembly, the tandem being separable from the bracket assembly. The bracket assembly may be configured to be locked to the shaft of the tandem and to the shaft of the ring colpostat in such a way that when locked, a distal end of the tandem remains in a fixed position relative to a distal end of the ring colpostat. The brachytherapy ring applicator may be configured such that all portions of the bracket assembly may be maintained outside a patient during treatment and no support mechanism may be provided between the bracket assembly and the distal end of the tandem or the distal end of the ring colpostat.

Example embodiments may be described in more detail below with reference to the appended figures.

BRIEF DESCRIPTION OF THE DRAWINGS

FIG. 28 shows a bottom view of the connecting shaft portion of the colpostat of the embodiment of FIG. 27.

FIG. 29 shows an enlarged portion of the bottom view of connecting shaft portion of the colpostat of FIG. 28.

FIG. 30 shows a front view of the connecting shaft portion of the colpostat of the embodiment of FIG. 27.

FIG. 31 shows an enlarged portion of the front view of connecting shaft portion of the colpostat of FIG. 30.

DETAILED DESCRIPTION

Figure 1:
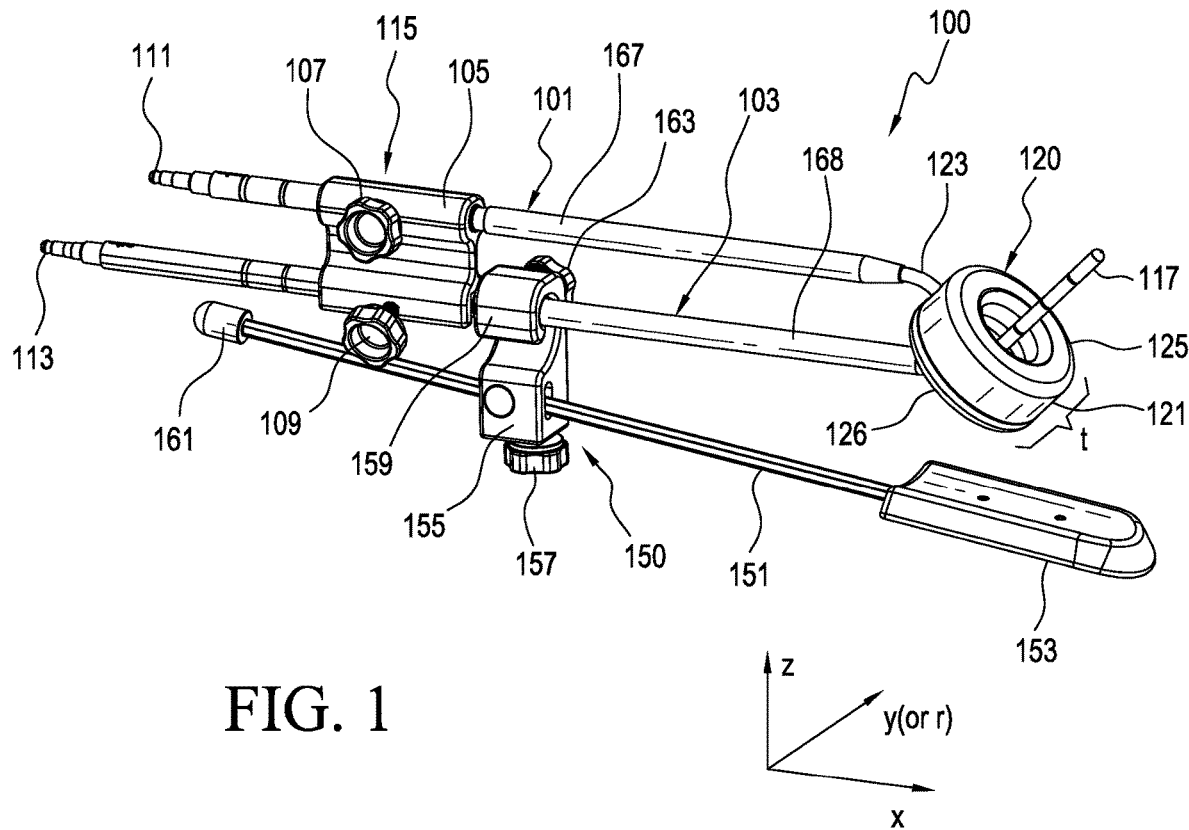
FIG. 1 shows a perspective view of a brachytherapy ring applicator assembly according to an embodiment.

In the detailed description, like reference characters denote like parts in the several figures, while not necessarily indicating that the parts of the several figures are of the same embodiment.

FIG. 1 shows a perspective view of a brachytherapy ring applicator assembly 100 according to a first embodiment. According to the embodiment, the brachytherapy ring applicator 100 may include a ring colpostat 101, a tandem 103, and a bracket assembly 115. The bracket assembly 115 may be configured to couple ring colpostat 101 to tandem 103. Ring colpostat 101 may include a ring member (covered by cap assembly 120) at a distal end and a connector 111 at a proximal end. Connector 111 may be connected to another apparatus or it may simply be covered. The ring colpostat

101 may include a shaft 167 extending from the connector 111 at the proximal end to the ring member (covered in this embodiment by cap assembly 120) at the distal end. The distal end of the ring colpostat 101 is opposite from the proximal end having connector 111. The ring member may be covered by cap assembly 120, which may include a first cap portion 121 and a second cap portion 126. A distal surface 125 of first cap portion 121 may be configured to be placed adjacent to an area to be treated with radiation, such as a cervix.

Further, tandem 103 of brachytherapy ring applicatory assembly 100 may include a shaft 168 extending from a connector 113, which is at the proximal end, to a treatment portion 117 arranged at a distal end. Shaft 168 may include a hollow tube having a channel formed therein (for example, see channel 131 in FIG. 7), through which a radiation source may pass to arrive at treatment portion 117 at the distal end and of the tandem, to provide radiation to the area to be treated. The connector 113 may be configured to be connected to a housing member of an afterloading system that feeds and withdraws the radiation source to the tandem and to the area to be treated, once the applicator may be positioned within the patient.

Brachytherapy ring applicatory assembly 100 may further include a bracket assembly 115 into which a connecting portion of the shaft 167 of the ring colpostat 101 and a connecting portion of the shaft 168 of the tandem 103 may be locked into place. The bracket assembly 115 may include a connector bracket 105 that may be completely and easily separable from both the shaft 167 of the ring colpostat 101 and the shaft 168 of the tandem 103. Because the connector bracket 105 and all components of the bracket assembly 115 (including locking screw 107 and 109) may be easily removed from the shaft 167 of the ring colpostat 101 and the shaft 168 of the tandem 103, the components of the bracket assembly 115 may be easily cleaned. A connecting portion of the shaft 167 of the ring colpostat 101 and a connecting portion of shaft 168 of the tandem 103 may be locked into channels (described herein) of the connector bracket 105 and locking screws 107 and 109 may be tightened to lock the ring colpostat 101 and the tandem 103 into a fixed position, respectively.

Figure 2:
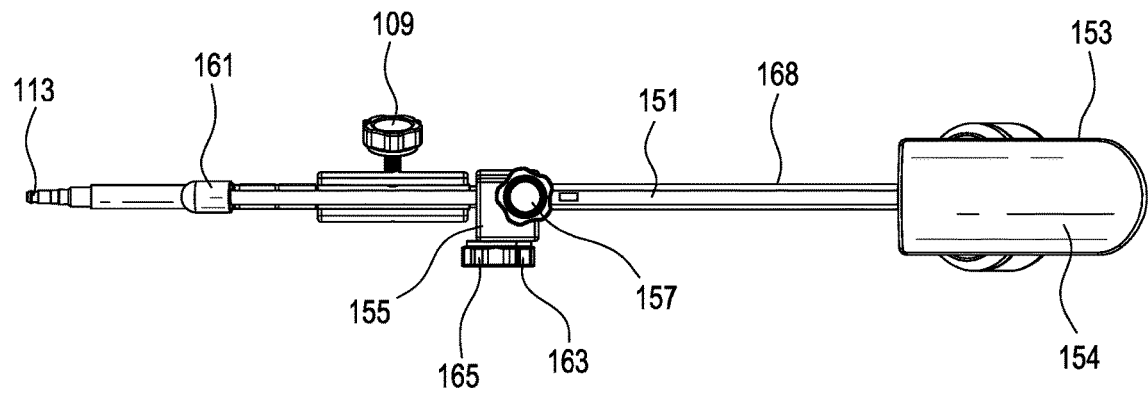
FIG. 2 shows a bottom view of the brachytherapy ring applicator assembly of FIG. 1.

The brachytherapy ring applicator assembly 100 may also include a rectal retraction assembly 150, which may include a rectal paddle 153, a rectal shaft 151, a knob 161, and a rectal assembly connector 155 that couples rectal shaft 151 to a portion of the brachytherapy ring applicator, such as to shaft 168 of tandem 103. For example, locking screw 157 may be used to lock a portion of the shaft 151 to the rectal assembly connector 155, and hook member 159 may be used to couple the rectal assembly connector 155 to a portion of the shaft 168 of the tandem. Locking screw 163 may be used to tight and lock the rectal assembly connector 155 to tandem 103. The angle of the rectal shaft 151 and length of the rectal shaft 151 may be adjusted by adjusting the locking screw 157 and a locking mechanism included in the rectal assembly connector 155, to apply a surface 154 of the rectal paddle, as shown in FIG. 2, to a portion of tissue to be retracted from the brachytherapy ring applicator 100. Such tissue, in this example, may include a posterior vaginal wall or a rectum area of the patient. Thus the rectal retraction assembly 150 reduces radiation exposure to the posterior vaginal wall and rectum of the patient and reduces harmful side effects to non-cancerous or healthy tissue that does not need to be treated with radiation. In place of, or in combination with, a rectal retraction assembly, packing or gauze may be employed to maintain distance between the brachytherapy ring application and radiation source and the rectum and posterior vaginal wall of the patient.

A cap assembly 120 may be connected to the ring member on the distal end of the ring colpostat 101 and provide proper alignment of the area to be treated, for example, the cervix of the patient. Cap assembly 120 may include a first cap part 121 and a second cap part 126, which may be connected to each other by threading one onto the other. The distance (t) provided by the cap assembly 120 may provide a more homogenous radiation exposure by increasing the distance of the radiation source provide in the treatment portion of the tandem and the area to be treated. Cap assemblies of varying thickness (t) may be provided to vary the distance between the radiation source the area to be treated.

Figure 3:
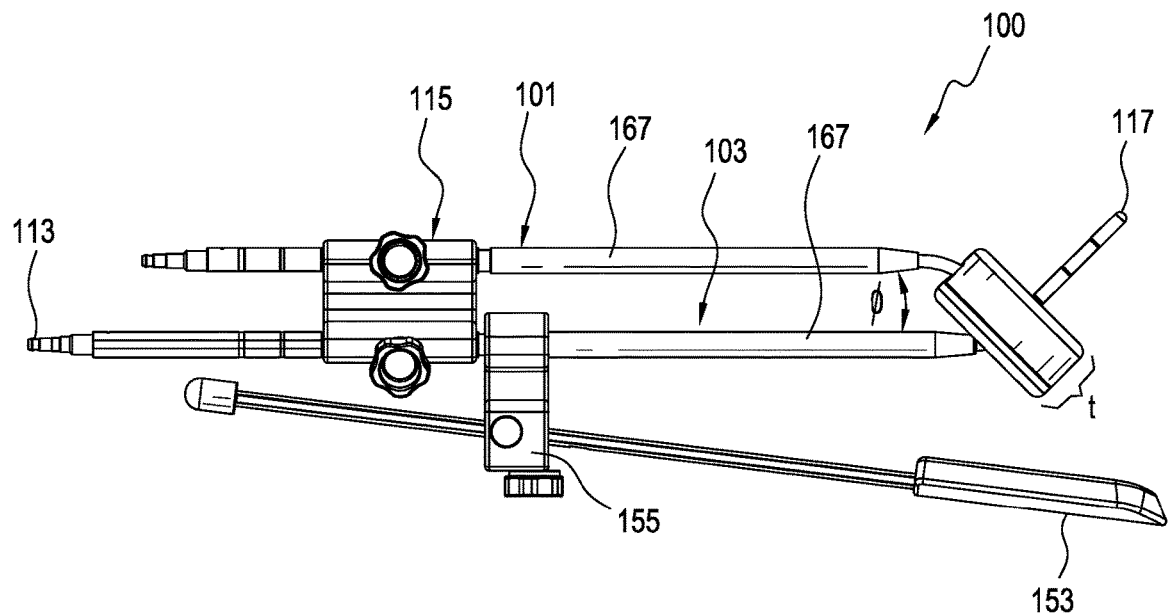
FIG. 3 shows a front view of the brachytherapy ring applicator assembly of FIG. 1.
Figure 4:
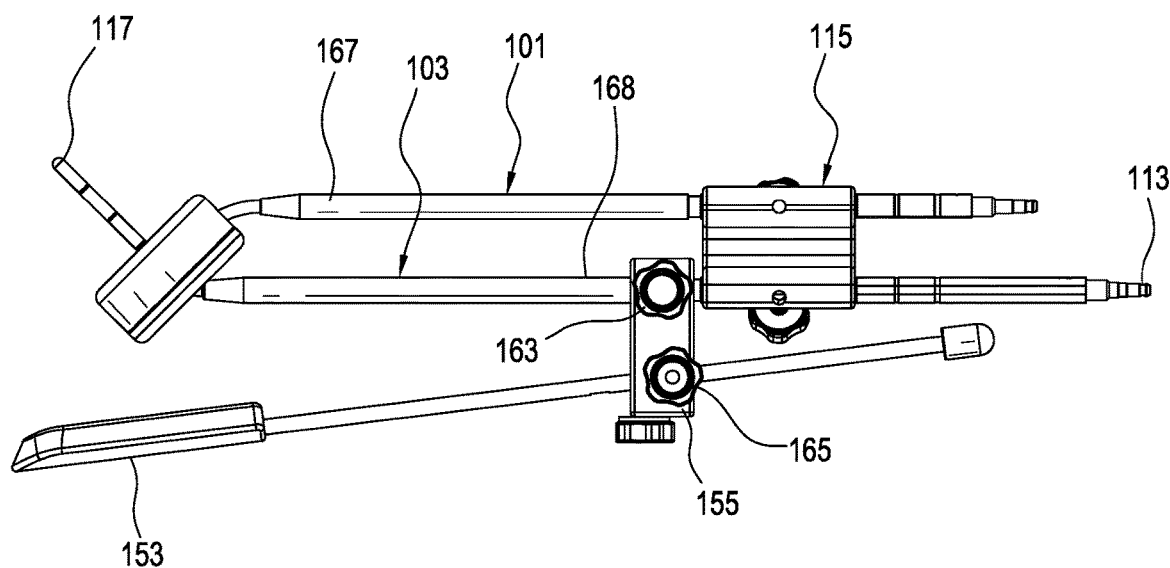
FIG. 4 shows a back view of the brachytherapy ring applicator assembly of FIG. 1.
Figure 5:
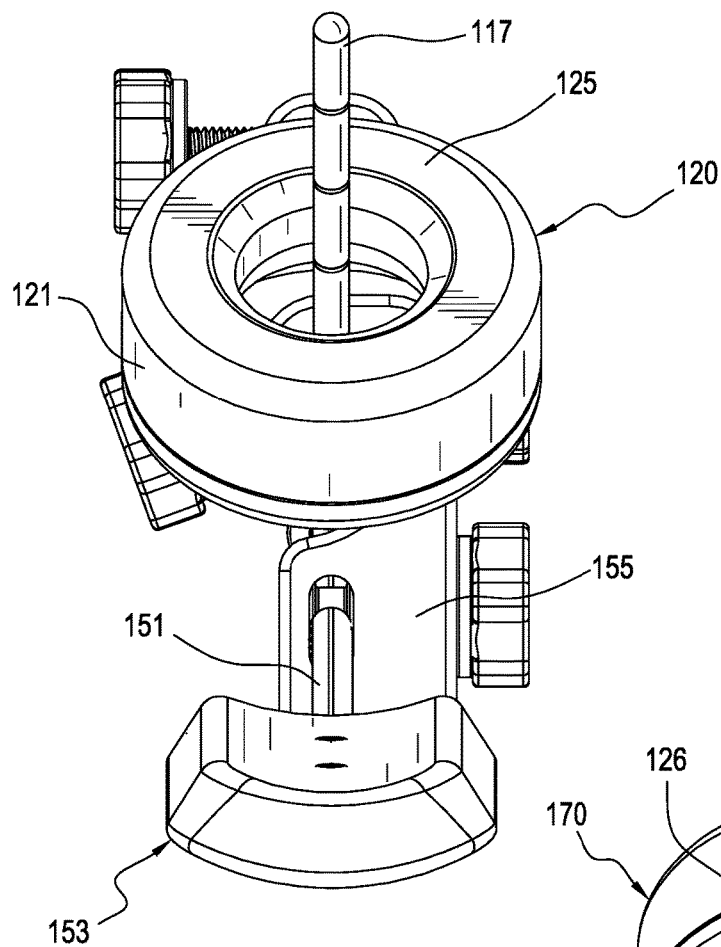
FIG. 5 shows a right-end view of the brachytherapy ring applicator assembly of FIG. 1.
Figure 6:
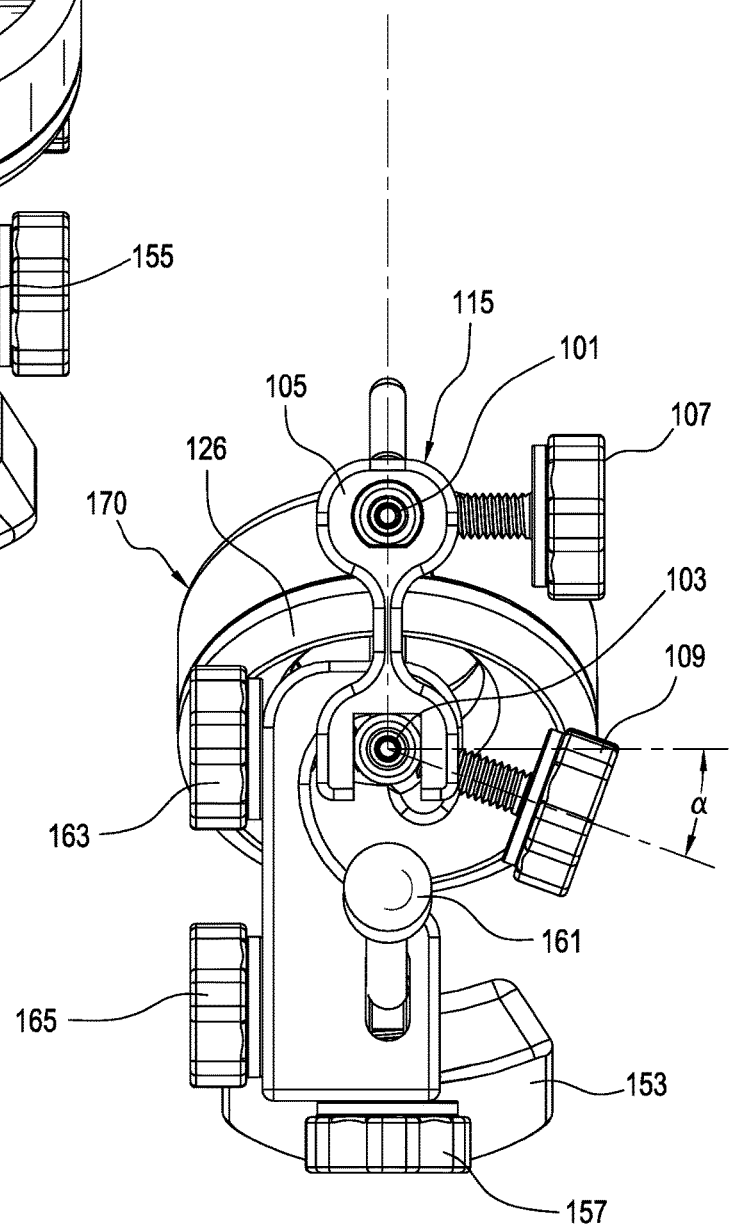
FIG. 6 shows a left-end view of the brachytherapy ring applicator assembly of FIG. 1.

FIG. 2 shows a bottom view of the brachytherapy ring applicator assembly of FIG. 1. FIG. 3 shows a front view of the brachytherapy ring applicator assembly of FIG. 1. FIG. 4 shows a back view of the brachytherapy ring applicator assembly of FIG. 1. FIG. 5 shows a right-end view of the brachytherapy ring applicator assembly of FIG. 1. FIG. 6 shows a left-end view of the brachytherapy ring applicator assembly of FIG. 1.

As shown in FIG. 6, the locking screw 109 may be provided at an offset angle ($\alpha$) from a direction perpendicular to the plane in which the shafts 167 and 168 of the ring colpostat 101 and the tandem 103. Offset angle ($\alpha$), which may be provided in the corresponding threaded locking portion of bracket connector 105 will be further explained herein as providing the locking force to maintain the connection portion of the shaft 168 of tandem 103 locked and fixed within an open channel of the connector bracket.

Figure 7:
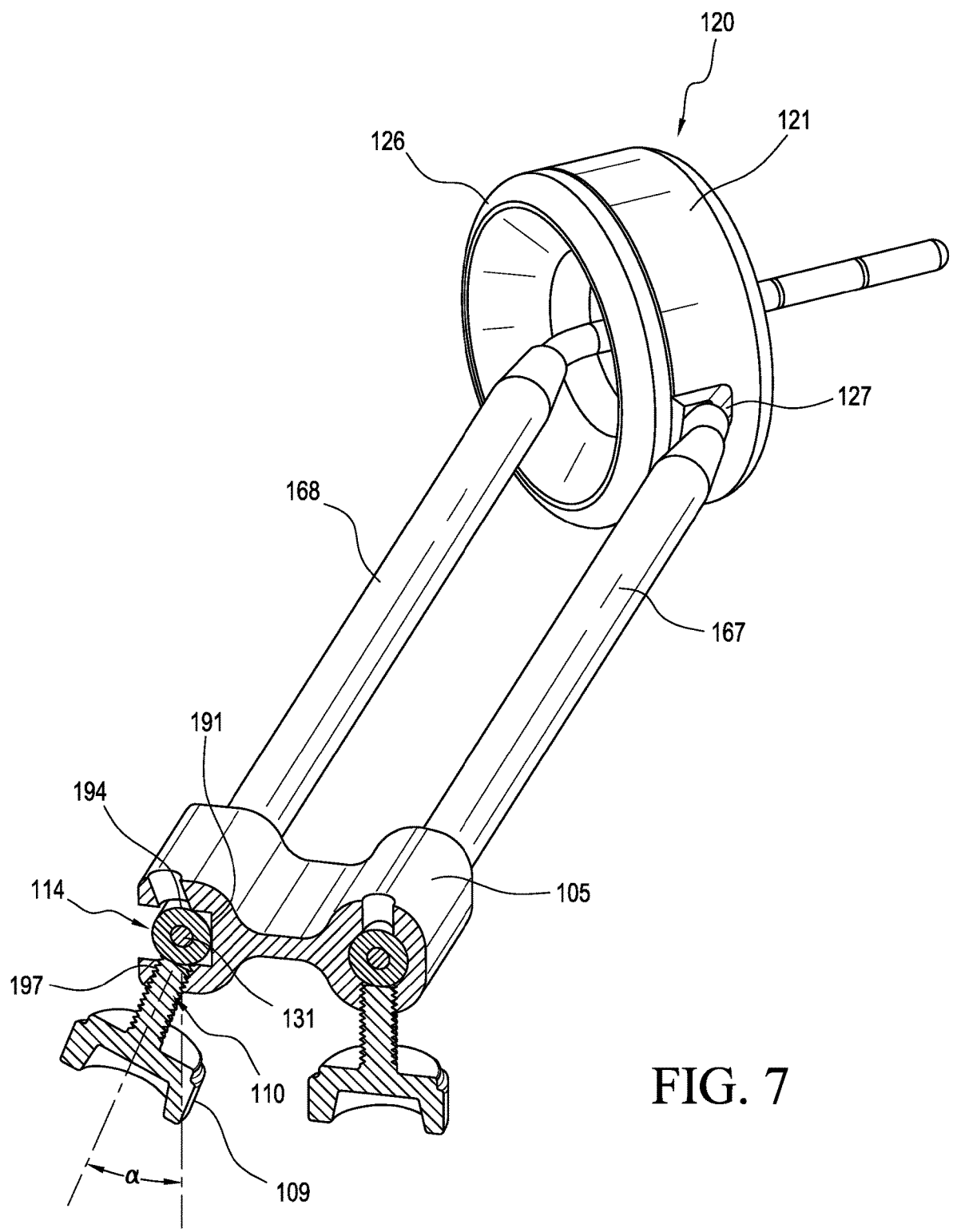
FIG. 7 shows a cross-sectional view of a brachytherapy ring applicator along a direction perpendicular to the axes of shafts of the ring colpostat and the tandem.

FIG. 7 shows a cross-sectional view of a brachytherapy ring applicator along a direction perpendicular to the axes of shafts of the ring colpostat 101 and the tandem 103. As shown in FIG. 7, connector bracket may include an open channel 114 in which a connecting portion of the shaft of the tandem 103 may be provided. Open channel 114 may be defined by a first connecting surface 191 and a second connecting surface 194, and threaded portion 110 of locking screw 109 may be screwed into corresponding locking threaded portion 197 formed in connector bracket 105, such that offset angle ($\alpha$) may be formed between an axis of the threaded locking portion and the plane in which the shafts of the tandem and ring colpostat lie. Thus, a locking force may be applied to the connecting portion of the shaft of the tandem, which pushes and locks the connecting portion of the shaft of the tandem against locking surfaces 191 and 194 and maintains the shaft 168 of the tandem within the open channel 114 of the connector bracket 105. FIG. 7 also shows cap opening 127, which allows passage of the ring member (not shown) within the cap assembly 120 including first cap part 121 and second cap part 126.

Figure 8:
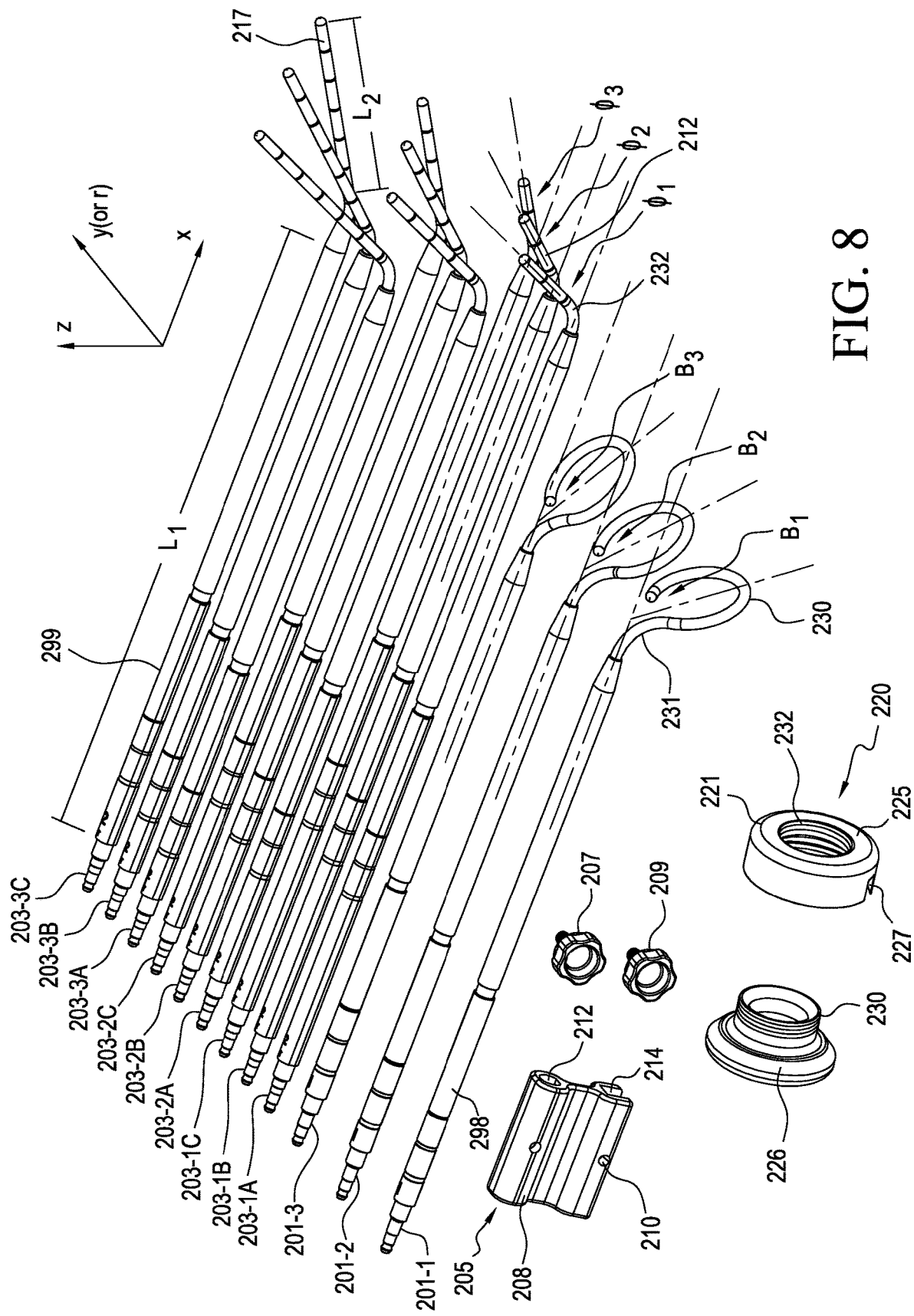
FIG. 8 shows a perspective view of an arrangement of various combinable components of a brachytherapy ring applicator assembly according to other embodiments.

FIG. 8 shows a perspective view of an arrangement of various combinable components of a brachytherapy ring applicator assembly kit according to other embodiments. According to the embodiments of the components shown in FIG. 8, various ring members may be provided 201-1, 201-2, 201-3, which have varying angles ($\beta 1$, $\beta 2$, $\beta 3$) of the plane of the ring members 230 with respect to the corresponding axes of the shafts of the ring colpostats 201-1, 201-2, 201-3, and angled portion 231 with the axes of the corresponding colpostats 201-1, 201-2, 201-3. Different angles ($\beta 1$, $\beta 2$, $\beta 3$) may be used depending on the positioning and presentation of the cervix of the patient, which may vary from patient to patient. Angles $\beta 1$, $\beta 2$, $\beta 3$ are shown in further detail in FIG. 10.

Additionally, various tandems 203-1A to 203-3C may be utilized of varying lengths L1 and with varying angles θ1, θ2, and θ3 formed at angled portion 232 of the tandem between the shaft of the tandem and the treatment portion 217 or distal end of the tandem. The offset angle (θ) between the treatment portion 217 or distal end of the tandem and the shaft of the tandem 103 may be, for example, 20°, 30°, 45°, or 60°, or within a range of 0° to 90° or within the range of 15° to 75°. Further, as shown the various tandems 203-1A to 203-3C, the length L2 of the treatment portion of the tandem may be varied, depending on the position within the cervix, cervical chamber, or uterus to be treated by the radiation, or the length of the cervix, cervical chamber, or uterus to be treated. Angles θ1, θ2, and θ3 are shown in greater detail in FIG. 10.

Locking screw 207 may be used to fasten a connecting portion 299 of a shaft of a tandem 203-3C within open channel 214. Locking screw 209 may be used to locking a connecting portion 298 of a shaft of a colpostat 201-1 within closed channel 212.

Cap assembly may include first cap part 226 and second cap part 221. Second cap part 221 may include threaded portion 232 to engage the threaded portion 230 of first cap part 226, and opening 227 may be provided to allow the second cap part 221 to fit onto ring member 230.

Figure 9:
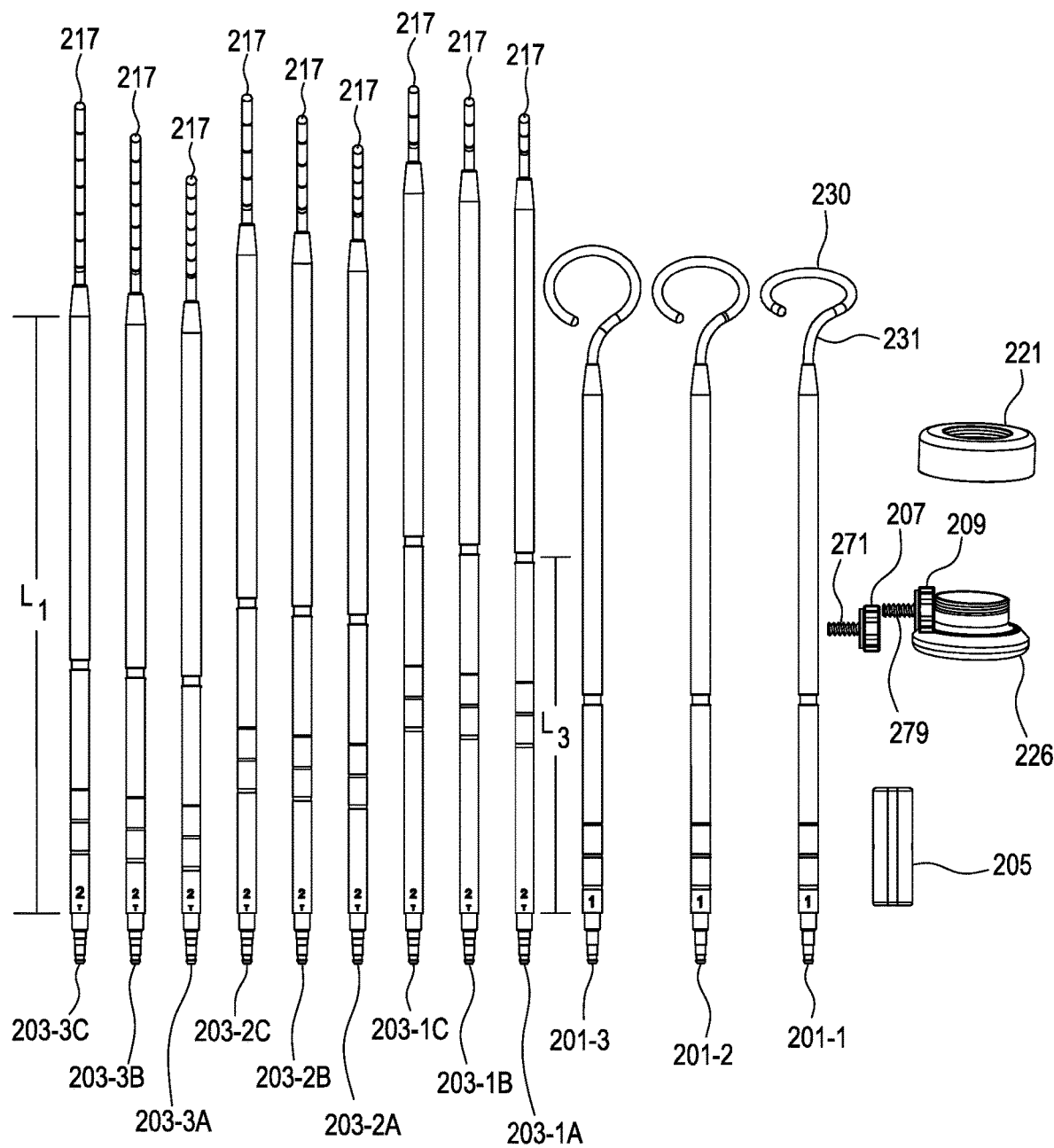
FIG. 9 shows a top view of the arrangement of various combinable components of a brachytherapy ring applicator assembly of the embodiments of FIG. 8.
Figure 10:
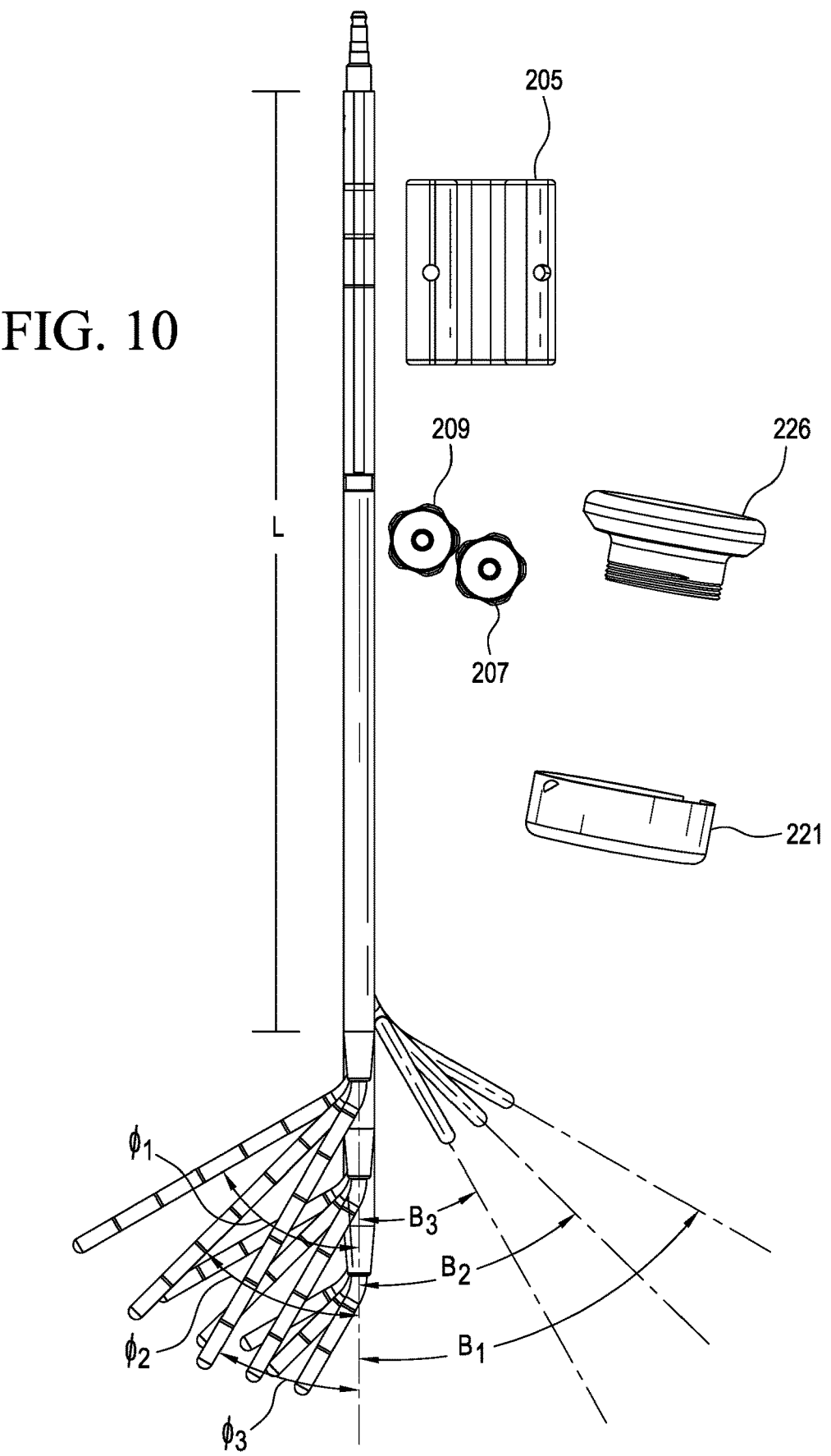
FIG. 10 shows a back view of the arrangement of various combinable components of a brachytherapy ring applicator assembly of the embodiments of FIG. 8.
Figure 11:
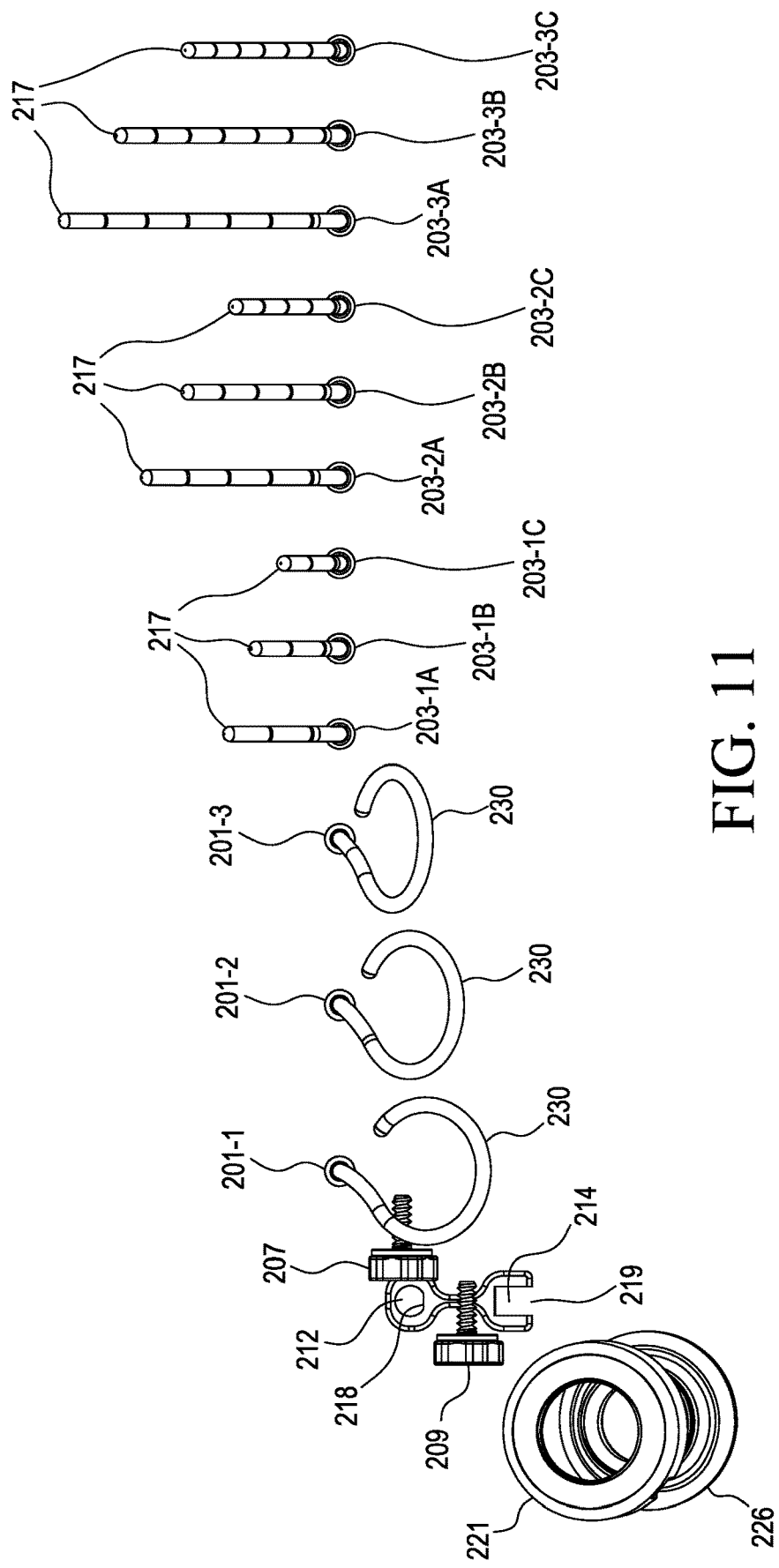
FIG. 11 shows a right-end view of the arrangement of various combinable components of a brachytherapy ring applicator assembly of the embodiments of FIG. 8.

FIG. 9 shows a top view of the arrangement of various combinable components of a brachytherapy ring applicator assembly kit of the embodiments of FIG. 8. Locking screws 207 and 209 have threaded shafts 217 and 219. FIG. 10 shows a back view of the arrangement of various combinable components of a brachytherapy ring applicator assembly kit of the embodiments of FIG. 8. FIG. 11 shows a right-end view of the arrangement of various combinable components of a brachytherapy ring applicator assembly kit of the embodiments of FIG. 8.

Figure 12:
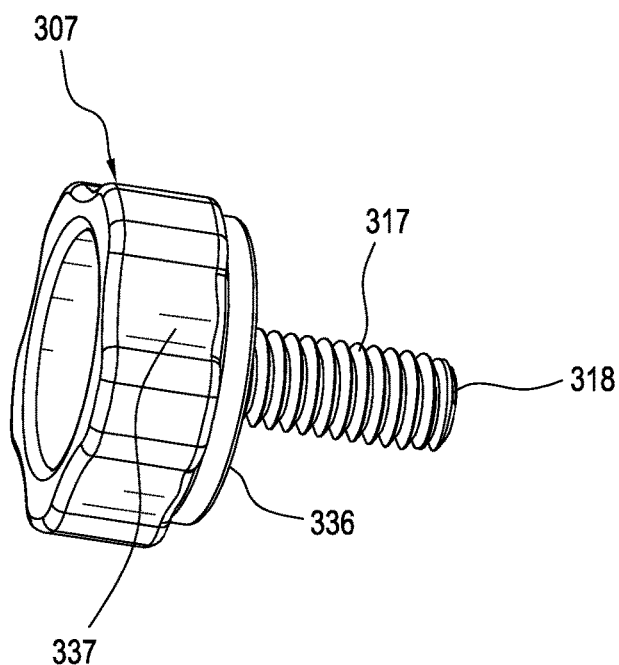
FIG. 12 shows an embodiment of a locking screw according to an embodiment.

FIG. 12 shows an embodiment of a locking screw 307 according to an embodiment, having threaded portion 317 and knob 337, which may be configured to be turned by one who administers the radiation treatment. Knob 337 may have an undersurface 336, and threaded portion 317 may have a distal end surface 318, which may be configured to come in forceful contact with an item to be locked in place, such as shaft 167 of ring colpostat 101 of a shaft 168 of the tandem 103 as knob 337 may be tightened by twisting.

Figure 13:
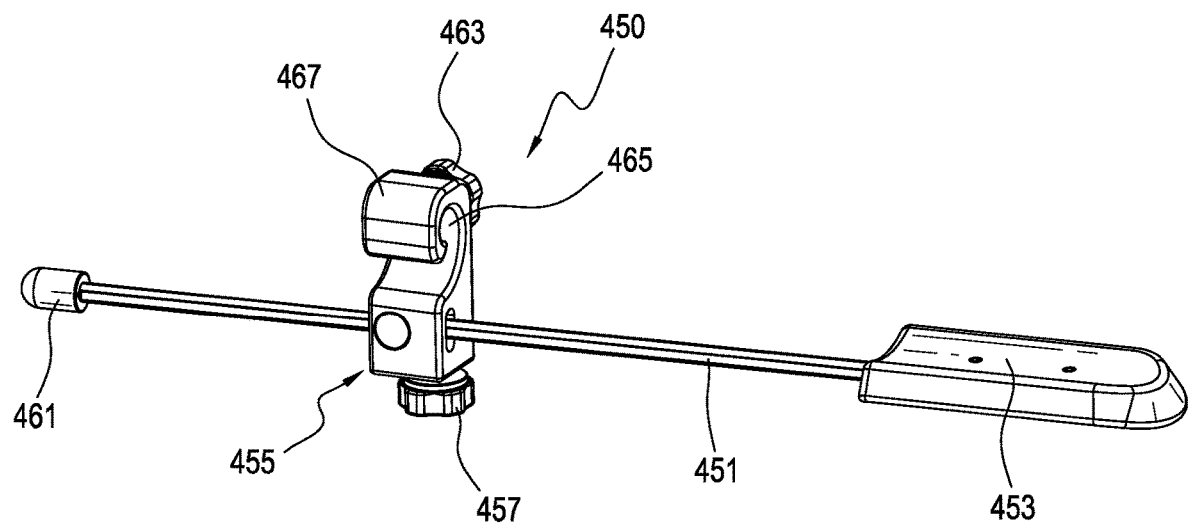
FIG. 13 shows a perspective view of a rectal paddle assembly according to another embodiment.

FIG. 13 shows a perspective view of a rectal paddle assembly according to another embodiment. The rectal paddle assembly may include a rectal paddle 453, a rectal shaft 451, a knob 461, and rectal assembly connector 455. Locking screw 457 may be used to lock a portion of the shaft 451 to the rectal assembly connector 455, and hook member 467 with curved inner surface portion 465 may be used to couple the rectal assembly connector 455 to a portion of a shaft of the tandem. Locking screw 463 may be used to tight and lock the rectal assembly connector a tandem. The angle of the rectal shaft 451 and length of the rectal shaft 451, that may be the distance between the rectal assembly connector and the rectal paddle, may be adjusted by adjusting the locking screw 457 and a locking mechanism include in the rectal assembly connector 455, to apply a surface 454 of the rectal paddle, as shown in FIG. 4C, to a portion of tissue to be retracted from the brachytherapy ring applicator 100. Such tissue, in this example, may include a posterior vaginal wall and rectum area of the patient. Thus the rectal retraction assembly reduces radiation exposure to the posterior vagina wall and rectum of the patient and reduces harmful side effects to non-cancerous or healthy tissue that does not need to be treated with radiation. In place of a rectal retraction assembly, or in combination with the rectal retraction assembly, packing or gauze may be employed to maintain distance between the brachytherapy ring application and radiation source and the rectum and posterior vaginal wall of the patient.

Figure 14:
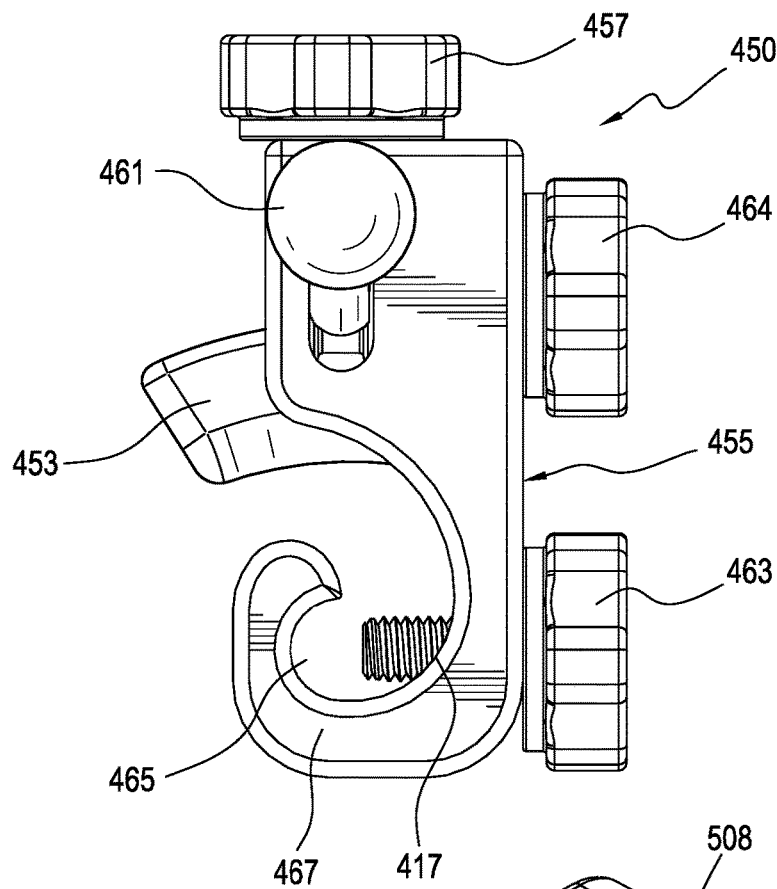
FIG. 14 shows a left-end view of the rectal paddle assembly of the embodiment of FIG. 13.

FIG. 14 shows a left-end view of the rectal paddle assembly of the embodiment of FIG. 13.

Figure 15:
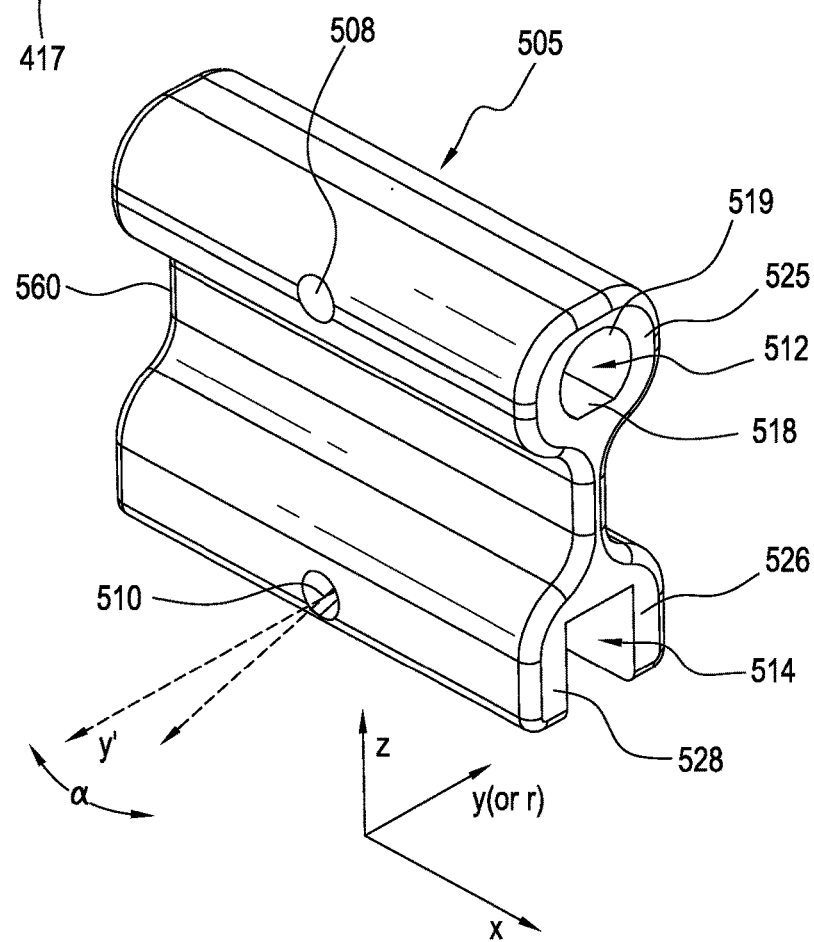
FIG. 15 shows a perspective view of a connector bracket according to another embodiment.
Figure 19:
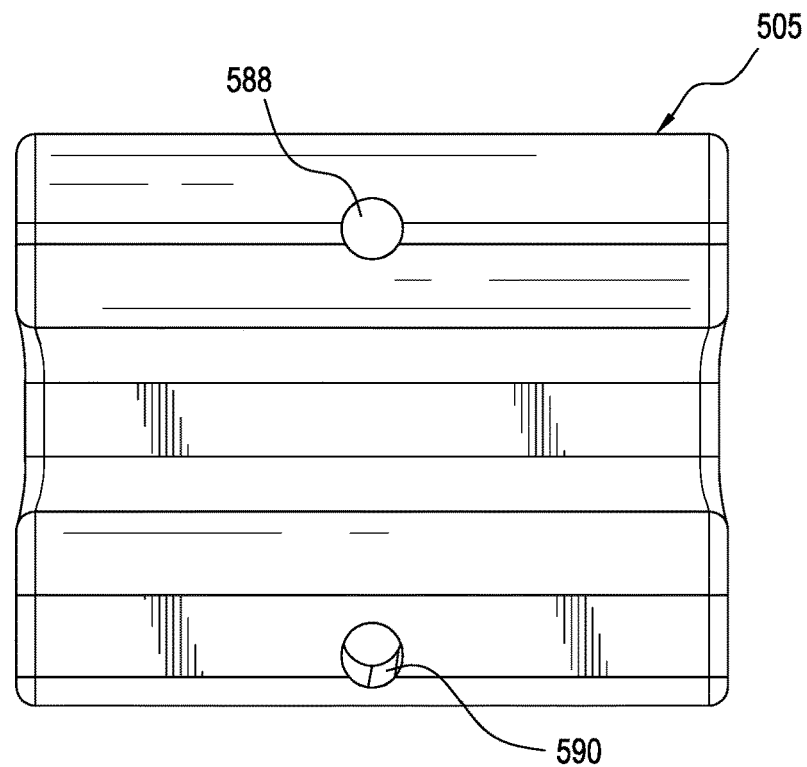
FIG. 19 shows a back view of the bracket of the embodiment of FIG. 15.

FIG. 15 shows a perspective view of a connector bracket 505 according to another embodiment. Connector bracket or bracket 505 may include a first channel 512, which may be a closed channel. Connector bracket 505 may include a second channel 514, which may be an open channel, meaning that on one side of the channel may be open to allow the bracket to be locked onto a connection portion of a shaft of a tandem by a movement of the connection portion of the tandem in a direction perpendicular to the axis of the shaft of the tandem. Locking holes 508 and 510 may be provided on one side of the connector bracket 505, and as shown in FIG. 19, locking holes 588 and 590 may be provided on the other side of connector bracket 505. Locking holes 508, 510, 588, and 590 may be tapped or threaded to receive threaded portions of a locking screw. By providing locking holes on each side of the connector bracket 505, the locking mechanism may be easily used by both right-handed and left-handed administrators of the brachytherapy radiation treatment. Both holes 510 and 590 may be offset from the plane in which the first and second channels extend by an angle α, as shown in FIG. 15.

Figure 16:
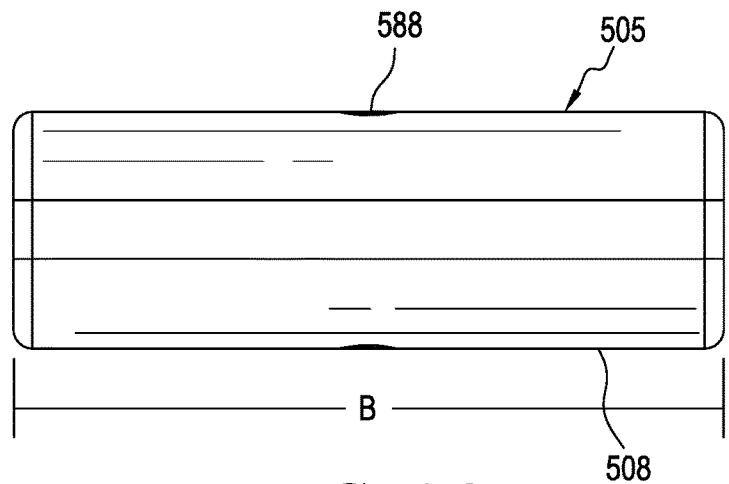
FIG. 16 shows a top view of the bracket of the embodiment of FIG. 15.
Figure 17:
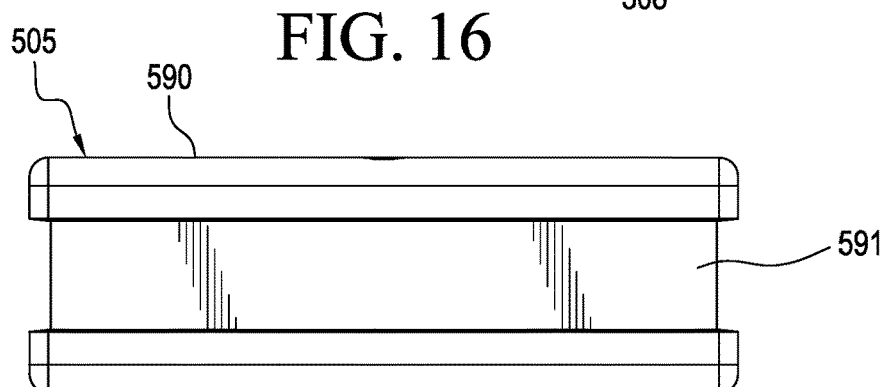
FIG. 17 shows a bottom view of the bracket of the embodiment of FIG. 15.
Figure 18:
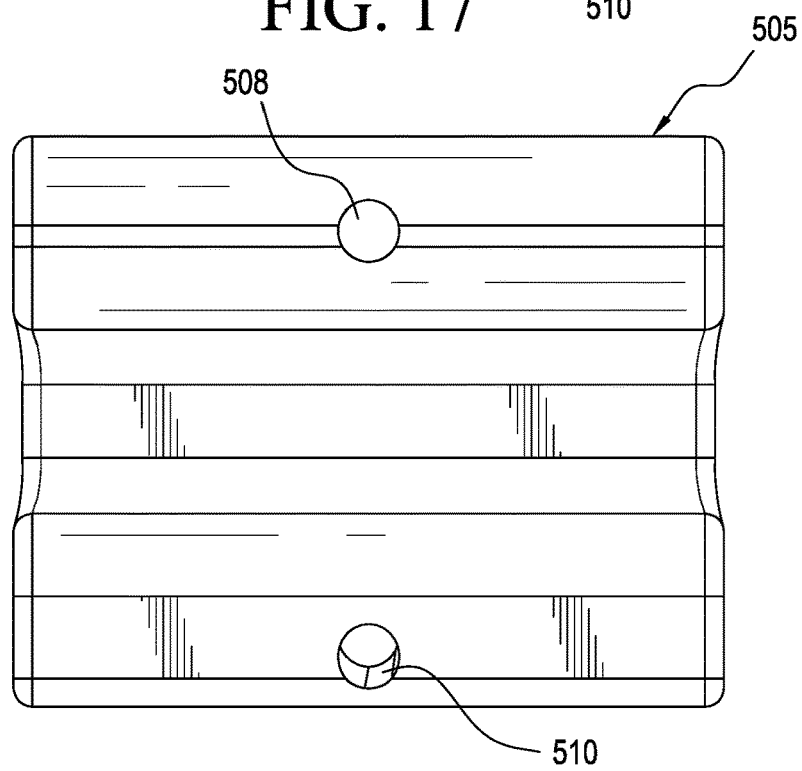
FIG. 18 shows a front view of the bracket of the embodiment of FIG. 15.
Figure 20:
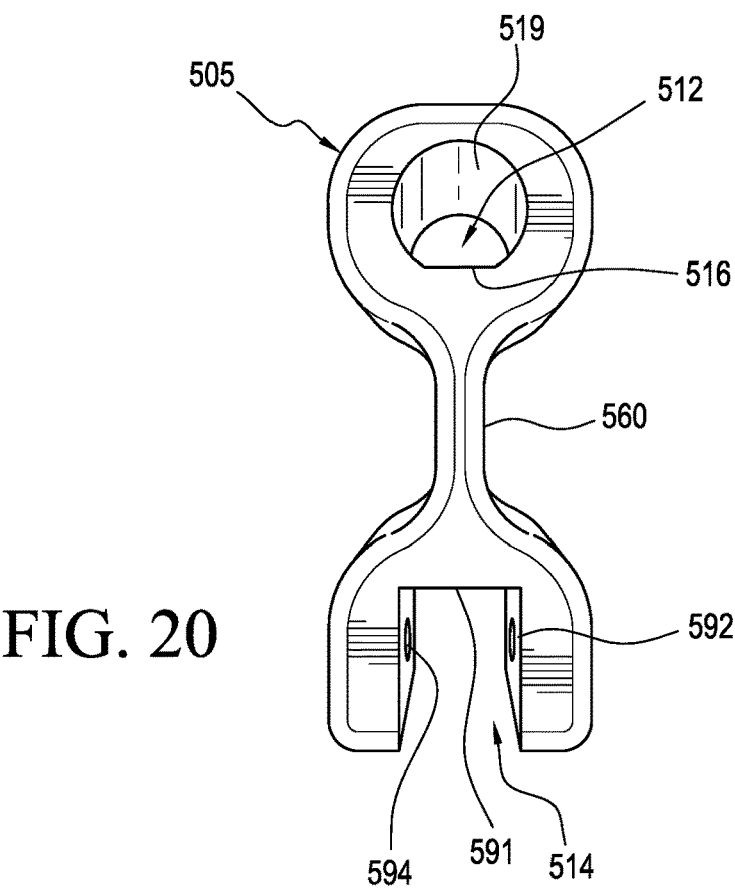
FIG. 20 shows a right-end view of the bracket of the embodiment of FIG. 15.

FIG. 16 shows a top view of the bracket of the embodiment of FIG. 15. FIG. 17 shows a bottom view of the bracket of the embodiment of FIG. 15. FIG. 18 shows a front view of the bracket of the embodiment of FIG. 15. FIG. 19 shows a back view of the bracket of the embodiment of FIG. 15. FIG. 20 shows a right-end view of the bracket of the embodiment of FIG. 15.

Figure 21:
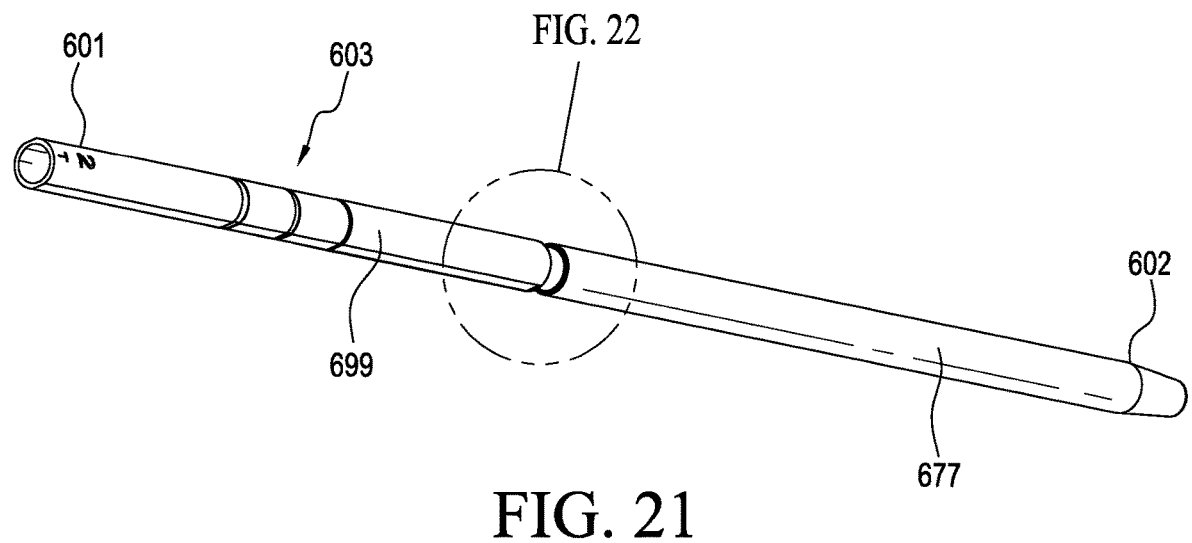
FIG. 21 shows a perspective view of a connecting shaft portion of a tandem according to another embodiment.
Figure 24:
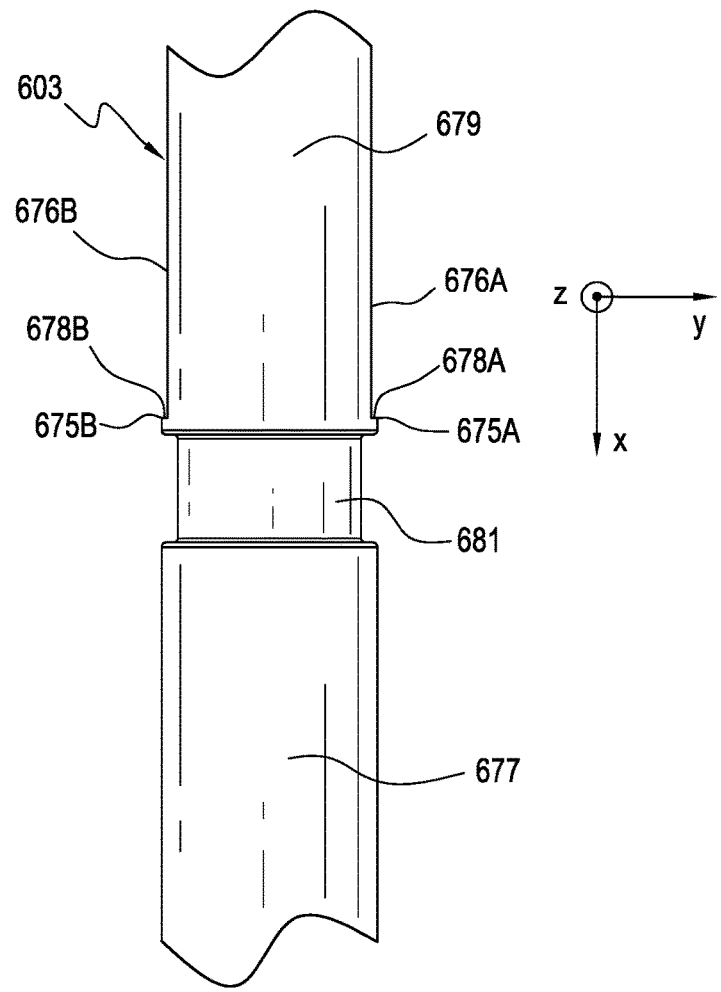
FIG. 24 shows an enlarged portion of the top view of the connecting shaft portion of the tandem of FIG. 23.

FIG. 21 shows a perspective view of a connecting shaft portion 699 of a shaft 677 of a tandem 603 according to another embodiment. According to the embodiment shown in FIG. 21, the connecting shaft portion 699 may be configured to be locked in the second or open channel 514 of connector bracket 505 as shown in FIGS. 15-20. As shown in the enlarged portion of FIG. 22, the connecting shaft portion 699 may include a radial stop mechanism, such as a radial locking surface 676A formed on a first side of the connecting shaft portion 699. In this embodiment, the radial locking surface 676A may be flat or relatively flat. A similar radial locking surface 676B may be formed on an opposite side of the connecting shaft portion 699, as shown in FIG. 24. Locking surfaces 676A and 676B may be configured to engage the inner locking surfaces 592 and 594 within open channel 514, as shown in FIG. 20. In this embodiment, the inner locking surfaces 592 and 594 may be flat or relatively flat.

The top round surface of connecting shaft portion 699 may be configured to come into contact with inner surface 591 of open channel 514. Additionally, each side of connecting shaft portion 699 (or at least one side) may include a stop members 675A, and may further include a second stop member 675B that protrude from the surface of radial locking surfaces 676A and 676B. Stop members 675A and 675B may have lateral stop surfaces 678A and 678B that may be configured to abut stop portions 526 and 528, respectively on connector bracket 505. With the aid of stop members 675A and 675B, when in contact with stop portions 526 and 528, the administrator of the radiation treatment can know with a surety the location of the treatment portion of the tandem within the patient, as the length of the tandem shaft may have been determined beforehand. Accordingly, the stop members 675A and 675B, when used with the corresponding stop portions 526 and 528 on the connector bracket significantly facilitate proper placement of the tandem and the bracket, which correlates to the position of the ring colpostat.

Additionally, groove 681, provided around a circumference of shaft portion 677 allows an administrator of the radiation treatment to feel the position of the shaft of the tandem, thus facilitating placement of the tandem within the connector bracket. Stop members 675A and 675B and correlating stop portions 526 and 528 thus prevent movement of the tandem in a direction parallel to the axis of the tandem with relation to the connector bracket 505 (the x direction in FIG. 1). And flat locking surfaces 676A and 676B, when in contact with stop surfaces 592 and 594, rotation of the tandem about its axis may be prevent, thus ensuring correct placement of the treatment portion of the tandem. As shown in FIG. 9, the length or the distance (L3) between the groove and the connector 213 of the various tandems (201-1A, 201-1B, . . . ) may vary. Thus, the length of the connecting shaft portion (and the corresponding lengths of the radial locking surfaces) may be varied to accommodate the anatomy of the patient to be treated.

Further, while it may be advantageous for the administrator of the radiation treatment to place the tandem such that stop surface(s) of the tandem are in contact with a corresponding surface of the connector bracket, with the aid of the groove 681, and a corresponding groove in the shaft of a corresponding colpostat (see groove 781 in FIG. 27), the administrator may be able to ascertain the relative spatial relationship between the distal ends of the tandem and colpostat without having to contact the stop surfaces of the colpostat and the tandem to the corresponding surface of the connector bracket.

Figure 22:
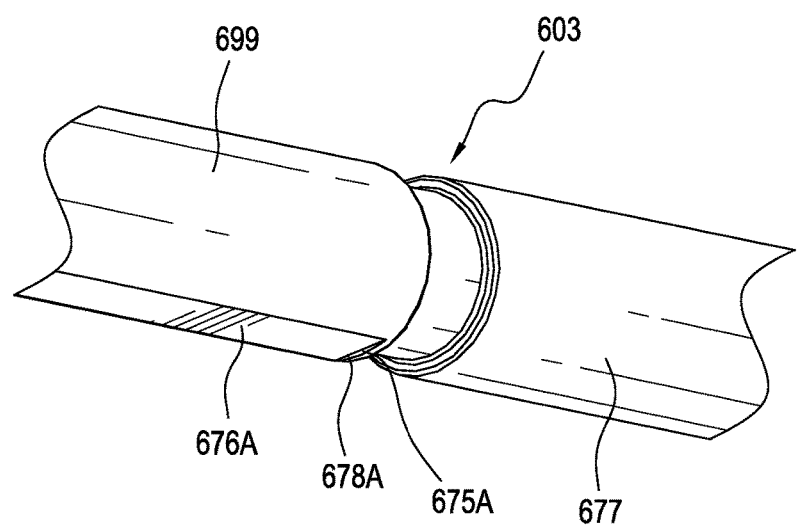
FIG. 22 shows an enlarged portion of the perspective view of the connecting shaft portion of the tandem of FIG. 21.
Figure 23:
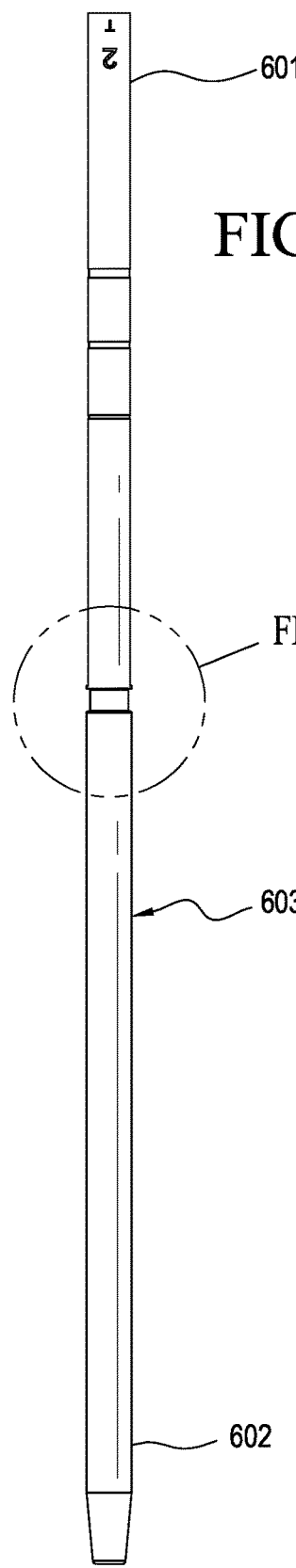
FIG. 23 shows a top view of the connecting shaft portion of the tandem of the embodiment of FIG. 21.
Figure 25:
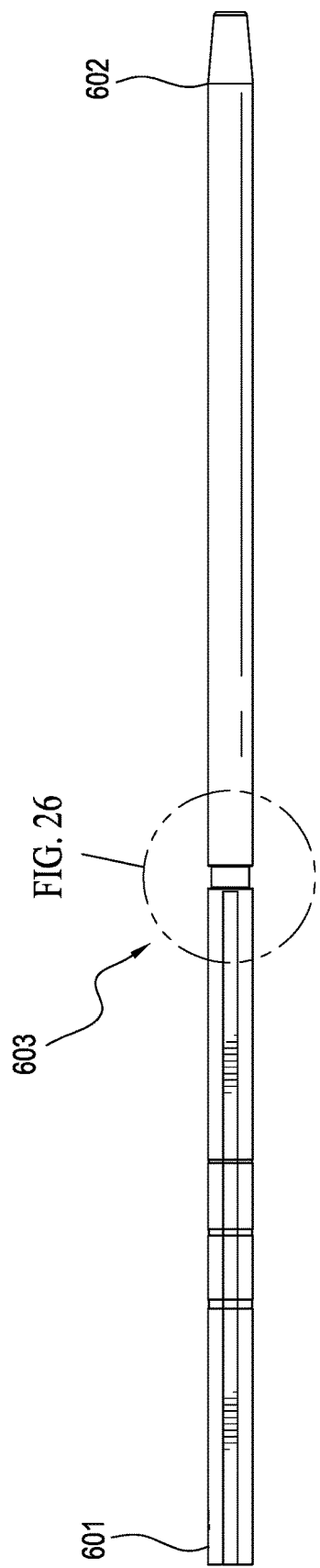
FIG. 25 shows a front view of the connecting shaft portion of the tandem of the embodiment of FIG. 21.
Figure 26:
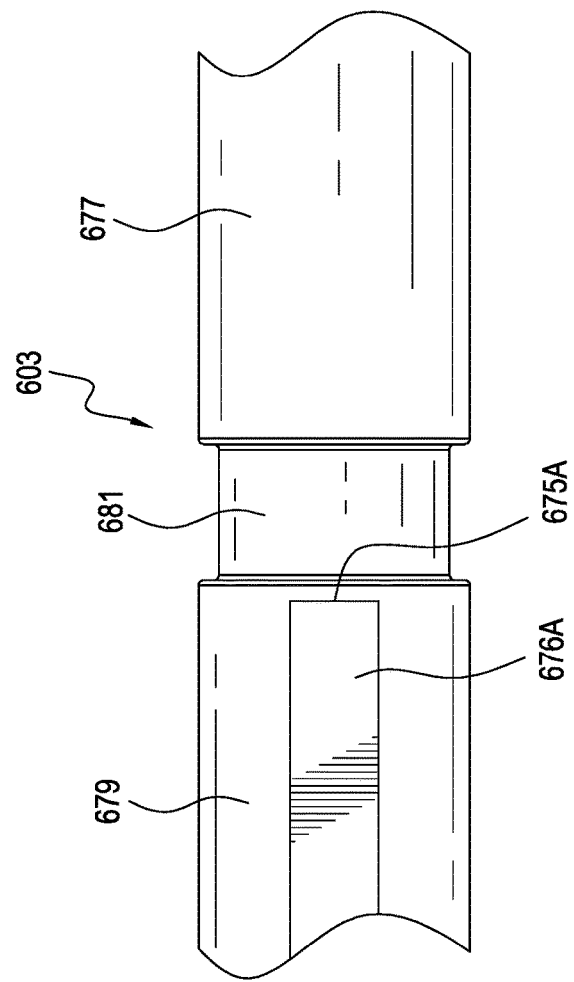
FIG. 26 shows an enlarged portion of the front view of the connecting shaft portion of the tandem of FIG. 25.

FIG. 22 shows an enlarged portion of the perspective view of the connecting shaft portion of the tandem of FIG. 21. FIG. 23 shows a top view of the connecting shaft portion of the tandem of the embodiment of FIG. 21. FIG. 24 shows an enlarged portion of the top view of the connecting shaft portion of the tandem of FIG. 23. FIG. 25 shows a front view of the connecting shaft portion of the tandem of the embodiment of FIG. 21. FIG. 26 shows an enlarged portion of the front view of the connecting shaft portion of the tandem of FIG. 25.

Figure 27:
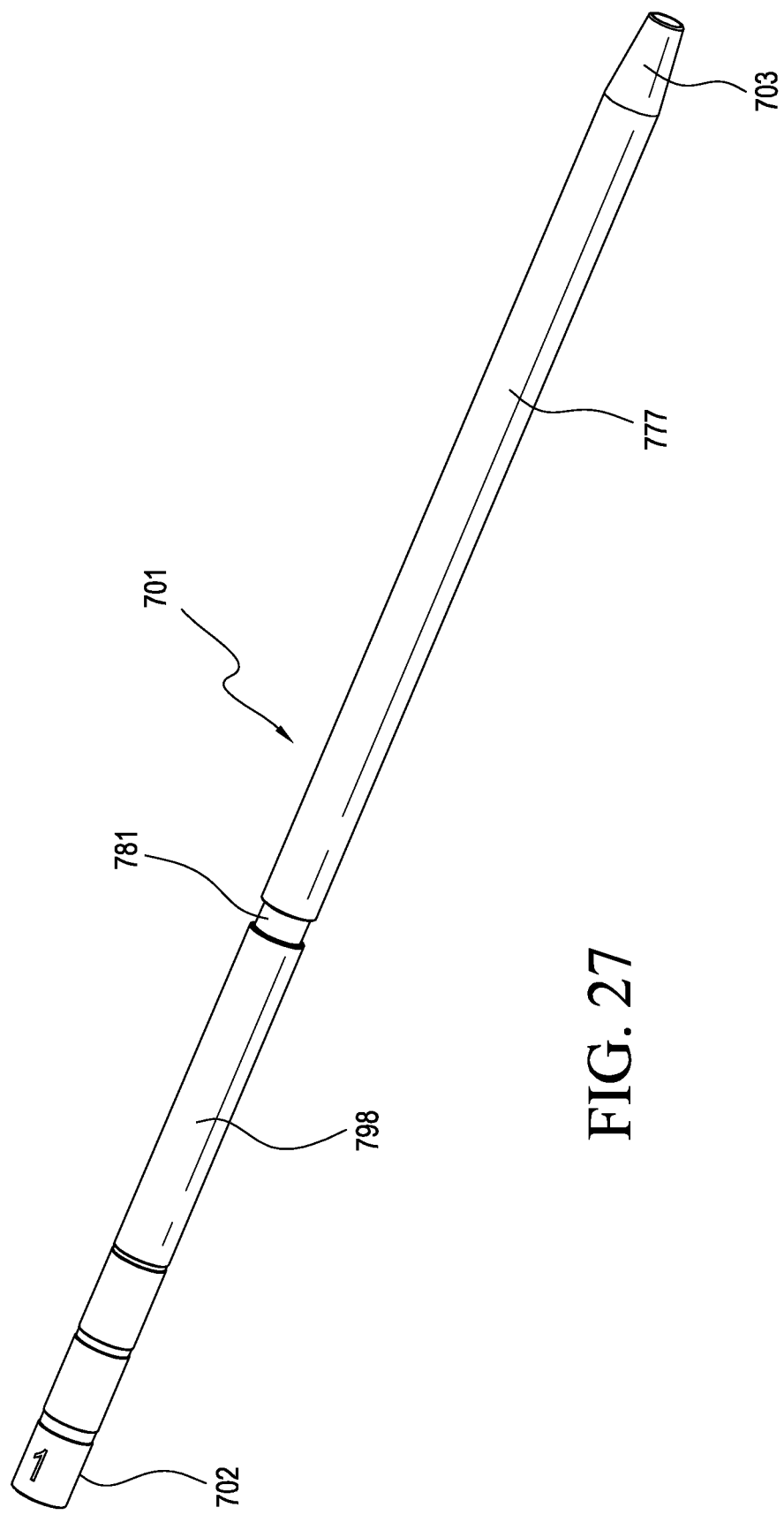
FIG. 27 shows a perspective view of a connecting shaft portion of a colpostat according to another embodiment.

FIG. 27 shows a perspective view of a connecting shaft portion 798 of a ring colpostat 701 according to another embodiment. The embodiment of FIGS. 27-31 may be configured to be locked into connector bracket 505 of FIGS. 15-20. As shown in FIGS. 28 and 29, connecting shaft portion 798 may have guide groove 781, to guide the administrator of the radiation treatment. Further, connecting shaft portion 798 may include flat locking surface 786 as a stop mechanism, which may be configured to come into contact with locking surface 518 of closed channel 512 of the connector bracket 505. Additionally, stop member 775 protrudes from flat locking surface and may include lateral surface 778 that may be configured to come into contact with stop surface 525 shown in FIG. 15. Thus, flat locking surface 776, when in contact with flat surface 518 prevents rotation of the shaft of the ring colpostat around its axis, and the contact of the lateral surface 778 with stop surface 525 prevents travel or movement of shaft of the ring colpostat in a direction parallel to the axis of the shaft of the ring colpostat (x direction in FIG. 1). Curved inner surface 519 of closed channel 512 may come into secure contact with the curved outer surface 779 of the connecting shaft portion 798.

When locked into place by threaded locking screw 107 through threaded locking portion 508, the ring colpostat can be locked in place securely. Similarly, locking screw 109 may secure the ring colpostat 701 in place, particularly at angle α, such that the shaft of the ring colpostat is locked into a firm position relative to the connector bracket 505 and other components of the applicator.

FIG. 28 shows a bottom view of the connecting shaft portion of the ring colpostat of the embodiment of FIG. 27. FIG. 29 shows an enlarged portion of the bottom view of ring connecting shaft portion of the colpostat of FIG. 28. FIG. 30 shows a front view of the connecting shaft portion of the ring colpostat of the embodiment of FIG. 27. FIG. 31 shows an enlarged portion of the front view of connecting shaft portion of the ring colpostat of FIG. 30.

A brachytherapy method for treating cancer may include the steps described herein, according to one embodiment. A shaft of a ring colpostat may be locked to a bracket assembly. Before locking the shaft of the ring colpostat, a cap assembly may be placed on a ring member of the ring colpostat. The ring colpostat may include the ring member on a distal end of the ring colpostat and the ring colpostat being separable from the bracket assembly. A tandem may be inserted into a patient, the tandem having a connector end on a proximal end of the tandem and a treatment end on a distal end of the tandem, the treatment end being configured to be arranged in proximity to the area to be treated by a radioactive source. The ring member of the ring colpostat may be then passed around the connector end of the tandem and the ring member may be passed along a shaft of the tandem to provide the ring member within proximity to the treatment end of the tandem and the proximity to the area to be treated. A shaft of the tandem may be locked to the bracket assembly, the tandem being separable from the bracket assembly. The bracket assembly may be configured to be locked to the shaft of the tandem and to the shaft of the ring colpostat in such a way that when locked, a distal end of the tandem remains in a fixed position relative to a distal end of the ring colpostat. The brachytherapy ring applicator may be configured such that all portions of the bracket assembly may be maintained outside a patient during treatment and no support mechanism may be provided between the bracket assembly and the distal end of the tandem or the distal end of the ring colpostat. A rectal retractor assembly, such as described herein, may be used to retract the rectum of the patient or packing may be used to retract the rectum of posterior vaginal wall of the patient. Then, the connector on the proximal end of the tandem may be connector to an afterloading apparatus, and through the afterloading apparatus, a radiation source may be placed at the treatment portion of the tandem.

Although in the above embodiments,

According to the embodiments described herein, with a connector bracket having a sufficient length B, for example, as shown in FIG. 16, and the protruding stop members of the connecting shaft portions of the ring colpostat and the tandem, and rotational locking provided by the flat locking surfaces of the ring colpostat and the tandem, the tandem and ring colpostat can be securely locked to the connector bracket while also being easily separable. By being so securely locked into position, an administrator of the radiation treatment may easily know that location of the treatment portion of the tandem relative to the ring member. Further, with a sufficiently rigid or self-supporting connector assembly and a sufficiently rigid or self-supporting shafts of each of the tandem and ring colpostat, no support mechanism or additional locking assembly would be required to be inserted within the patient. In this past, this has been problematic, as the ring colpostat and tandem of previously known brachytherapy ring applicators have been maintained in position, relatively to each other by a connecting portion that is inserted within the orifice of the patient. For example, previously known brachytherapy ring applicators have included a ring colpostat and a tandem connected to each by a bracket assembly and an additional support member such that the additional support member. With such brachytherapy applicators, when the ring colpostat is connected to the tandem, the additional support member is located within the vaginal area, for example, between the vaginal walls. This has been particularly problematic, as the tandem is often inserted into a patient before the tandem is coupled to colpostat. Accordingly, with previously known brachytherapy ring applicators, the alignment of the additional support member, which is often located between connecting assembly and the distal ends of the ring colpostat and the tandem, is not visible to the administrator of the brachytherapy treatment. Because the additional support member is not visible, it is difficult to properly align and connect components of the additional support member. Accordingly the brachytherapy ring applicator described in the embodiments herein, the tandem can be inserted into the patient (for example, inserted into the vagina) and the colpostat can be then be inserted, and with both the tandem and the colpostat inserted, the tandem and the colpostat can be much more easily joined such that the shafts of the colpostat and the tandem are parallel or relatively parallel, without a change in the angle between the two shafts (shown in φ in FIG. 3), may be kept constant during the radiation treatment. Or alternatively, the colpostat can be inserted within the patient before the tandem is inserted. Further, previously known brachytherapy ring applicators having additional support members positioned within the orifice of the patient are significantly disadvantageous, as such applicators require further cleaning of the often intricate surfaces of the additional support members.

Additionally, according to previously known brachytherapy ring applicators, the coupling portions may be not separable from the tandem and ring colpostat, but may be immovably fixed thereto. Such an arrangement makes cleaning of the brachytherapy assembly more difficult after treatment. Finally, because the known brachytherapy applicators require placement of the support member within the vagina during use, the support members can easily become misaligned upon coupling of the coupling parts, while such misalignment may be not visible to the administrator of the radiation treatment due to the positioning of the support members within the vagina.

Further, the ring colpostat, tandem, and connecting bracket of the brachytherapy ring applicator of this disclosure are able to be completely separated. However, the configuration of connector bracket and the corresponding locking surfaces on the connecting portion of both the tandem and the colpostat can be properly aligned with respect to each other much more easily due to the corresponding internal surfaces of the connector bracket. And due to the lateral stop surfaces formed at an end portion of the locking surfaces on the connecting portions of both the tandem and the colpostat, it can easily be ensured that the distal end portions of the tandem and the colpostat are arranged at the proper length relative to each other and the connector bracket, due to the stop surfaces of the connector bracket.

These problems are addressed and overcome according to the embodiments of the brachytherapy ring applicator described herein.

Although specific embodiments may be described herein, various different mechanisms could be used to achieve the same effect. For example, threaded locking screw of the connector bracket assembly could be replaced with locking pins, springs, or cotters.

Additionally, in the above embodiments, the inner locking surfaces 592 and 594 and locking inner surface 591 may be flat or relatively flat, and the corresponding radial locking surfaces 676A and 676B, and 786 are corresponding flat or relatively flat, in other embodiments, the inner locking surfaces of the connector bracket and corresponding radial locking surfaces of the connecting portions of the tandem and colpostat may be of a different contour. For example, as shown in the connector bracket 1105 of FIG. 32A, the inner locking surface 1118 of the first channel 1112, which is configured to mate with the shaft of the ring colpostat, may have a slightly concave contour with a radius of curvature different than the radius of curvature of the other inner surface portion 1117 and of the other outer surface of a cylindrical portion of the connecting portion of the shaft of the ring colpostat. Alternatively, or in addition to the channel 1112 having a concave inner locking surface 1118 with a radius of curvature different than that of the other portion of the shaft of the colpostat, the connector bracket may also have a second channel 1114, which is configured to mate with a connecting portion of a shaft of a tandem, wherein the second channel 1114 includes another concave inner locking surface 1191 that is configured to mate with a convex radial locking surface on the connecting portion of the shaft of the corresponding tandem.

Figures 32A, 32B, 32C:
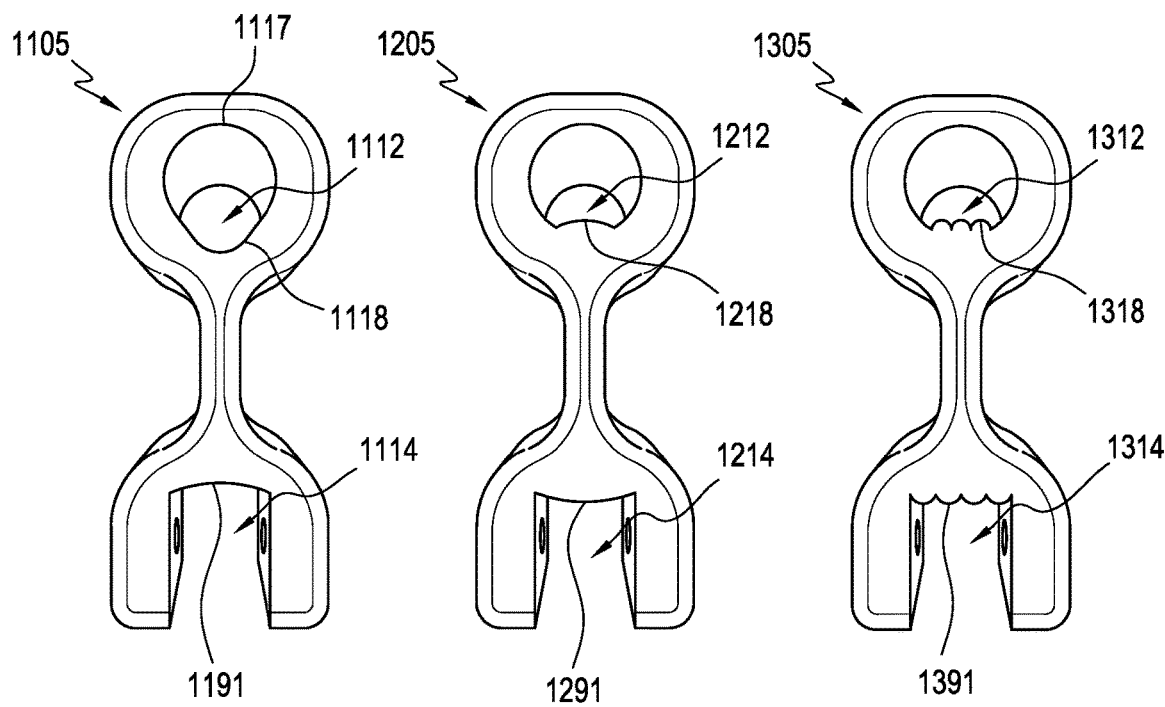
FIG. 32A shows a connector bracket according to another embodiment.
FIG. 32B shows a connector bracket according to another embodiment.
FIG. 32C shows a connector bracket according to another embodiment.

Or, as shown in FIG. 32B, a connector bracket 1205 may have a closed channel 1212 configured to mate with a shaft of the ring colpostat wherein the channel 1212 includes an inner locking surface 1218 that is convex. A brachytherapy ring applicatory assembly with such a connector bracket 1205 would have a ring colpostat having a shaft with a radial locking surface having a corresponding concave radial locking surface. Alternatively, or in addition to the channel 1212 having a convex inner locking surface 1218, the connector bracket may also have a second channel 1214, which is configured to mate with a connecting portion of a shaft of a tandem, wherein the second channel 1214 includes a convex inner locking surface 1291 that is configured to mate with a concave radial locking surface on the connecting portion of the shaft of the corresponding tandem.

Or in the alternative embodiment of FIG. 32C, a connector bracket 1305 may have a closed channel 1312 configured to mate with a shaft of the ring colpostat wherein the channel 1312 includes an inner locking surface 1218 that having one or more ridges or grooves. A brachytherapy ring applicatory assembly with such a connector bracket 1305 would have a ring colpostat having a shaft with a radial locking surface having a corresponding grooved or ridged radial locking surface. Alternatively, or in addition to the channel 1312 having an inner locking surface 1318 with ridges or grooves, the connector bracket may also have a second channel 1314, which is configured to mate with a connecting portion of a shaft of a tandem, wherein the second channel 1314 includes a convex inner locking surface 1391 that is configured to mate with a grooved or ridged radial locking surface on the connecting portion of the shaft of the corresponding tandem.

Figures 32D, 32E, 32F:
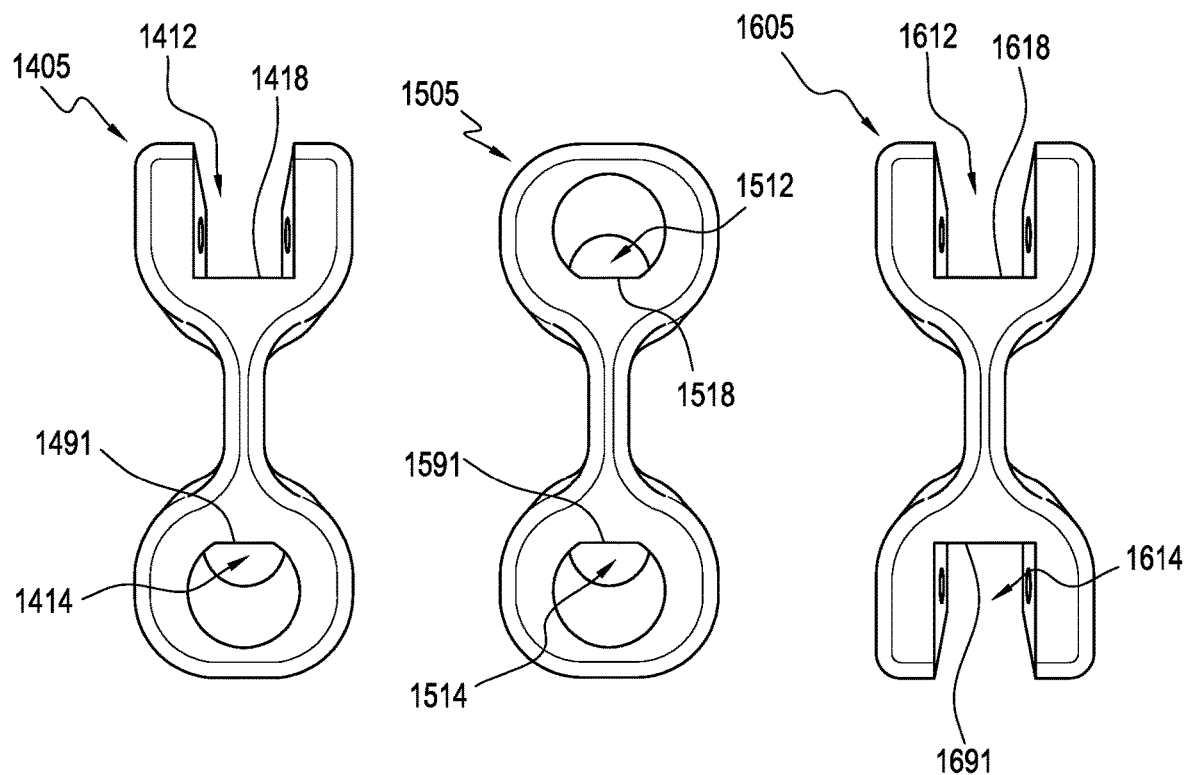
FIG. 32D shows a connector bracket according to another embodiment.
FIG. 32E shows a connector bracket according to another embodiment.
FIG. 32F shows a connector bracket according to another embodiment.

In yet another embodiment, as shown in FIG. 32D, a connector bracket 1405 may have a first channel 1412 that is configured to mate with a shaft of a corresponding colpostat, wherein the first channel 1412 is an open channel, while a second channel 1414 of the connector bracket 1405 is a closed channel configured to made with a shaft of a corresponding tandem.

And in anther embodiment, as shown in FIG. 32E, a connector bracket 1505 may have a first channel 1512 that is configured to mate with a shaft of a corresponding colpostat, wherein the first channel 1512 is closed channel, while a second channel 1514 of the connector bracket 1505 is also a closed channel configured to made with a shaft of a corresponding tandem.

Alternatively, as shown in FIG. 32F, a connector bracket 1605 may have a first channel 1612 that is configured to mate with a shaft of a corresponding colpostat, wherein the first channel 1612 is an open channel, while a second channel 1614 of the connector bracket 1405 is also an open channel configured to made with a shaft of a corresponding tandem.

In other embodiments, the corresponding inner locking surfaces of the first or second channels are some permutation of the above embodiments, with corresponding radial locking surfaces on the connecting portion of the shaft of the corresponding colpostat or tandem. What is advantageous is that the contour of the locking surfaces of the connecting portions of the and the corresponding surfaces within the channels of the connecting bracket contact each other so as to prevent rotation of the tandem or ring colpostat about the axis of their shafts when the ring colpostat or the tandem is coupled to the bracket connector. Other means could further be considered with respect to the protruding stop members and the corresponding contact surfaces and locking surfaces of the connector bracket. By being placed in contact with corresponding inner locking surfaces 592 and 594, locking surfaces 676A and 676B prevent rotation of the tandem 603 about the axis of the shaft 677. Further, the corresponding inner and radial locking surfaces of the connector bracket and the connecting shaft portion, respectively, provide for easy and proper alignment of the tandem 603 with respect to the connector bracket, and to other components of the applicator, such as a colpostat.

In addition, the present disclosure may be configured as described below.

1. A brachytherapy ring applicator comprising:
a tandem having a connector end on a proximal end of the tandem and a treatment end on a distal end of the tandem, the treatment end being configured to be arranged in proximity to the area to be treated by a radioactive source;
a ring colpostat including a ring member on a distal end of the ring colpostat, the ring member being configured to position the treatment end of the tandem; and
a bracket assembly is configured to be locked to both a shaft of the tandem and to a shaft of the ring colpostat such that the distal end of the tandem is firmly maintained in a fixed position relative to the distal end of the ring colpostat, and wherein the tandem, the colpostat, and the bracket assembly are configured such that, when the tandem and the ring colpostat are locked to the bracket assembly, the tandem, from a location of attachment of the shaft of the tandem to the bracket assembly to the distal end of the tandem, and the colpostat, from the location of attachment of the shaft of the colpostat to the bracket assembly to the distal end of the colpostat, are entirely self-supporting.

2. The brachytherapy ring applicator according to any one or more of 1 above or 3 to 18 below, wherein the bracket assembly is detachable from the tandem and from the ring colpostat.

3. The brachytherapy ring applicator according to any one or more of 1 or 2 above or 4 to 18 below, wherein all portions of the bracket assembly are arranged to be maintained outside a patient during treatment and no additional support mechanism is provided between the bracket assembly and the distal end of the tandem or the distal end of the ring colpostat.

4. The brachytherapy ring applicator according to any one or more of 1 to 3 above or 5 to 18 below, wherein the bracket assembly is configured such when locked to the bracket assembly, the shaft of the tandem and the shaft of the ring colpostat are substantially parallel.

5. The brachytherapy ring applicator according to any one or more of 1 to 4 above or 6 to 18 below, wherein the bracket assembly includes a connector bracket having a first channel and a second channel, the first channel being configured to be locked to a connecting portion of the shaft of the tandem and the second channel are configured to be locked to a connecting portion of the shaft of the ring colpostat.

6. The brachytherapy ring applicator according to any one or more of 1 to 5 above or 7 to 18 below, wherein
the bracket assembly includes a first locking mechanism configured to maintain the connecting portion of the shaft of the tandem fixed within the first channel without movement of the shaft of the tandem in either a radial or axial direction in relation to the bracket assembly, and
the bracket assembly includes a second locking mechanism configured to maintain the connecting portion of the shaft of the ring colpostat fixed within the second channel without movement of the shaft of the ring colpostat in either a radial or axial direction in relation to the bracket assembly.

7. The brachytherapy ring applicator according to any one or more of 1 to 6 above or 8 to 18 below, wherein the tandem includes a radial stop mechanism provided on a shaft of the tandem, the radial stop mechanism of the tandem being configured to engage a locking portion of the bracket assembly to prevent movement around an axis of the shaft of the tandem when the radial stop mechanism of the tandem is engaged with a connector bracket of the bracket assembly.

8. The brachytherapy ring applicator according to any one or more of 1 to 7 above or 9 to 18 below, wherein the tandem includes an axial stop member provided on a connecting portion of the tandem, the axial stop member being configured to in a direction parallel with the axis of the shaft of the tandem when the axial stop member is engaged with a connector bracket of the bracket assembly.

9. The brachytherapy ring applicator according to any one or more of 1 to 8 above or 10 to 18 below, wherein the radial stop mechanism of the tandem includes a flat radial-locking surface formed in the connecting portion of the shaft of the tandem, the flat radial-locking surface being formed in a plane extending parallel to the axis of the tandem, and the stop mechanism of the tandem further includes an axial stop surface being perpendicular or nearly perpendicular to the flat radial-locking surface, and
wherein the connector bracket includes a corresponding flat radial-locking surface configured to engage and contact the flat radial-locking surface of the tandem when the tandem is locked to the connector bracket.

10. The brachytherapy ring applicator according to any one or more of 1 to 9 above or 11 to 18 below, wherein the bracket assembly includes a separable threaded locking screw and a corresponding threaded locking portion formed in the connector bracket, the corresponding threaded locking portion being configured to receive the separable threaded locking screw, wherein the threaded locking portion has an axis arranged at an angle offset from perpendicular to a plane in which the shaft of the tandem and the shaft of the ring colpostat extend, such that the threaded locking screw contributes a locking force to maintain the connecting portion of shaft of the tandem within an open channel in which the shaft of the tandem is locked.

11. The brachytherapy ring applicator according to any one or more of 1 to 10 above or 12 to 18 below, wherein the ring colpostat includes a radial stop mechanism provided on a shaft of the ring colpostat, the radial stop mechanism of the ring colpostat being configured to engage a locking portion of the bracket assembly to prevent movement around an axis of the shaft of the ring colpostat when the radial stop mechanism of the ring colpostat is engaged with a connector bracket of the bracket assembly.

12. The brachytherapy ring applicator according to any one or more of 1 to 11 above or 13 to 18 below, wherein the ring colpostat includes an axial stop member provided on a connecting portion of the ring colpostat, the axial stop member being configured to in a direction parallel with the axis of the shaft of the ring colpostat when the axial stop member is engaged with a connector bracket of the bracket assembly.

13. The brachytherapy ring applicator according to any one or more of 1 to 12 above or 14 to 18 below, wherein the radial stop mechanism of the ring colpostat includes a flat radial-locking surface formed in the connecting portion of the shaft of the ring colpostat, the flat radial-locking surface being formed in a plane extending parallel to the axis of the ring colpostat, and the stop mechanism of the tandem further includes an axial stop surface being perpendicular or nearly perpendicular to the flat radial-locking surface, and wherein the connector bracket includes a corresponding flat radial-locking surface configured to engage and contact the flat radial-locking surface of the ring colpostat when the ring colpostat is locked to the connector bracket.

14. The brachytherapy ring applicator according to any one or more of 1 to 13 above or 15 to 18 below, wherein the ring colpostat includes a radial stop mechanism provided on a shaft of the ring colpostat, the radial stop mechanism of the ring colpostat being configured to engage a locking portion of the bracket assembly to prevent movement around an axis of the shaft of the ring colpostat when the radial stop mechanism of the ring colpostat is engaged with a connector bracket of the bracket assembly,
the ring colpostat includes an axial stop member provided on a connecting portion of the ring colpostat, the axial stop member being configured to in a direction parallel with the axis of the shaft of the ring colpostat when the axial stop member is engaged with a connector bracket of the bracket assembly,
the radial stop mechanism of the ring colpostat includes a flat radial-locking surface formed in the connecting portion of the shaft of the ring colpostat, the flat radial-locking surface being formed in a plane extending parallel to the axis of the ring colpostat, and the stop mechanism of the tandem further includes an axial stop surface being perpendicular or nearly perpendicular to the flat radial-locking surface, and wherein the connector bracket includes a corresponding flat radial-locking surface configured to engage and contact the flat radial-locking surface of the ring colpostat when the ring colpostat is locked to the connector bracket.

15. The brachytherapy ring applicator according to any one or more of 1 to 14 above or 16 to 18 below, wherein the shaft of the tandem and the shaft of the ring colpostat are sufficiently rigid such that in the case that a connecting portion of the shaft of the tandem and a connecting portion of the shaft of the ring application is locked to the bracket assembly, the shaft of the tandem and the shaft of the ring colpostat remain substantially parallel and the distal end of the tandem remains in a fixed position relative to the distal end of the ring colpostat while the tandem and the ring colpostat are inserted into a patient.

16. The brachytherapy ring applicator according to any one or more of 1 to 15 above or 17 or 18 below, further comprising a rectal assembly including a rectal paddle, a rectal shaft, and rectal connector,
wherein the rectal paddle is configured to engage a posterior vaginal wall of a patient and retract a rectal region from the tandem and colpostat, the rectal paddle extending distally from the rectal shaft and the rectal connector connecting the rectal paddle and the rectal shaft to the shaft of the tandem.

17. The brachytherapy ring applicator according to any one or more of 1 to 16 above or 18 below,
wherein the bracket assembly includes a separable threaded locking screw and a corresponding first threaded locking portion formed in a first side of the connector bracket and a corresponding second threaded locking portion formed in a second side of the connector bracket, the first side of the connector bracket being opposite from the second side of the connector bracket, the corresponding first threaded locking portion and the corresponding second threaded locking portion each being configured to receive the separable threaded locking screw, and
wherein the corresponding first threaded locking portion and the corresponding second threaded locking portion each have an axis arranged at an angle offset from perpendicular to a plane in which the shaft of the tandem and the shaft of the ring colpostat extend, such that each of the corresponding first threaded locking portion and the corresponding second threaded locking portion each the threaded locking screw, upon receiving the threaded locking screw contributes a locking force to maintain the connecting portion of shaft of the tandem within an open channel in which the shaft of the tandem is locked.

18. The brachytherapy ring applicator according to any one or more of 1 to 17 above, wherein the connector end of the tandem is configured to be coupled to an afterloading apparatus, and the treatment end includes a treatment portion extending in a direction offset from an axis of the shaft of the tandem by a first angle, and
the ring member extends in a direction offset from an axis of the shaft of the ring application by a second angle.

19. A brachytherapy ring applicatory kit comprising:
a plurality of tandems according to any one or more of 1 to 18 above, each of the tandems having a connector end on a proximal end of the tandem and a treatment end on a distal end of the tandem, the treatment end being configured to be arranged in proximity to the area to be treated by a radioactive source;
a plurality of ring colpostats according to any one or more of 1 to 18 above, each of the ring colpostats including a ring member on a distal end of the ring colpostat, the ring member being configured to position the treatment end of the tandem; and
a bracket assembly according to any one or more of 1 to 18 above, wherein the bracket assembly is configured to be locked both to both a shaft of one of said plurality of tandems and to a shaft of one of said ring colpostats such that the distal end of said one of said tandems is firmly maintained in a fixed position relative to the distal end of said one of said ring colpostats,
wherein said tandems, colpostats, and bracket assembly are configured such that, when one of said tandems and one of said ring colpostats are locked to the bracket assembly, said one of said tandems, from a location of attachment of the shaft of said tandem to the bracket assembly to the distal end of said tandem, and said one of said colpostats, from the location of attachment of the shaft of said colpostat to the bracket assembly to the distal end of said colpostat, are entirely self-supporting.

20. A brachytherapy method for treating cancer using a brachytherapy ring applicator according to any one or more of 1 to 18 above, the method comprising the steps of: locking a shaft of a ring colpostat to a bracket assembly, the ring colpostat including a ring member on a distal end of the ring colpostat, the ring colpostat being separable from the bracket assembly;

inserting a tandem into a patient, the tandem having a connector end on a proximal end of the tandem and a treatment end on a distal end of the tandem, the treatment end being configured to be arranged in proximity to the area to be treated by a radioactive source;

passing the ring member of the ring colpostat around the connector end of the tandem and passing the ring member along a shaft of the tandem to provide the ring member within proximity to the treatment end of the tandem and the proximity to the area to be treated;

locking a shaft of the tandem to the bracket assembly, the tandem being separable from the bracket assembly;

wherein the bracket assembly is configured to be locked to both the shaft of the tandem and to the shaft of the ring colpostat such that the distal end of the tandem is firmly maintained in a fixed position relative to the distal end of the ring colpostat, and wherein the tandem, the colpostat, and the bracket assembly are configured such that the tandem, when the tandem and the ring colpostat are locked to the bracket assembly, the tandem, from a location of attachment of the shaft of the tandem to the bracket assembly to the distal end of the tandem, and the colpostat, from the location of attachment of the shaft of the colpostat to the bracket assembly to the distal end of the colpostat, are entirely self-supporting.

While various embodiments of the present invention have been described above, and although various examples and experiments disclosing various aspects of the present invention have been disclosed, it should be understood that they have been presented by way of example only, and not limitation. Various changes in form and details may be made therein without departing from the spirit and scope of the invention as defined in the appended claims. Accordingly, the breadth and scope of the present invention should not be limited by any of the above-described exemplary embodiments, but should be defined only in accordance with the following claims and their equivalents.

The invention claimed is:

1. A brachytherapy ring applicator comprising:
a tandem having a connector on a proximal end of the tandem and a treatment end on a distal end of the tandem, the treatment end being configured to be arranged in proximity to the area to be treated by a radioactive source;
a ring colpostat including a ring member on a distal end of the ring colpostat, the ring member being configured to position the treatment end of the tandem; and
a bracket assembly configured to be locked to both a shaft of the tandem and to a shaft of the ring colpostat such that the distal end of the tandem is firmly maintained in a fixed position relative to the distal end of the ring colpostat,
wherein said tandem, said colpostat, and said bracket assembly are configured such that, when the tandem and the ring colpostat are locked to the bracket assembly, the tandem, from a location of attachment of the shaft of the tandem to the bracket assembly to the distal end of the tandem, and the colpostat, from the location of attachment of the shaft of the colpostat to the bracket assembly to the distal end of the colpostat, are entirely self-supporting,
wherein the bracket assembly includes a connector bracket having a first channel, the first channel being an open channel configured to be locked to a connecting portion of the shaft of the tandem, and
wherein the bracket assembly includes a separable threaded locking screw and a corresponding first threaded locking portion formed in the connector bracket, the first threaded locking portion being configured to receive the separable threaded locking screw, wherein the threaded locking portion has an axis arranged at an angle offset from perpendicular to a plane in which the shaft of the tandem and the shaft of the ring colpostat extend, such that the threaded locking screw contributes a locking force to maintain the connecting portion of the shaft of the tandem within the first channel.

2. The brachytherapy ring applicator according to claim 1, wherein the bracket assembly is detachable from the tandem and from the ring colpostat.

3. The brachytherapy ring applicator according to claim 1, wherein all portions of the bracket assembly are arranged to be maintained outside a patient during treatment and no additional support mechanism is provided between the bracket assembly and the distal end of the tandem or the distal end of the ring colpostat.

4. The brachytherapy ring applicator according to claim 1, wherein the bracket assembly is configured such when locked to the bracket assembly, the shaft of the tandem and the shaft of the ring colpostat are substantially parallel.

5. The brachytherapy ring applicator according to claim 1, wherein
the connector bracket further includes a second channel, the second channel being a closed channel configured to be locked to a connecting portion of the shaft of the ring colpostat.

6. The brachytherapy ring applicator according to claim 5, wherein the bracket assembly includes:
a first locking mechanism configured to maintain the connecting portion of the shaft of the tandem fixed within the first channel without movement of the shaft of the tandem in either a radial or axial direction in relation to the bracket assembly, and
a second locking mechanism configured to maintain the connecting portion of the shaft of the ring colpostat fixed within the second channel without movement of the shaft of the ring colpostat in either a radial or axial direction in relation to the bracket assembly.

7. The brachytherapy ring applicator according to claim 1, wherein the tandem includes a radial stop mechanism provided on the shaft of the tandem, the radial stop mechanism of the tandem being configured to engage a locking portion of the bracket assembly to prevent movement around an axis of the shaft of the tandem when the radial stop mechanism of the tandem is engaged with the connector bracket of the bracket assembly.

8. The brachytherapy ring applicator according to claim 7, wherein the tandem includes an axial stop member provided on the connecting portion of the tandem, the axial stop member being configured to prevent movement in a direction parallel with the axis of the shaft of the tandem when the axial stop member is engaged with the connector bracket of the bracket assembly.

9. The brachytherapy ring applicator according to claim 8, wherein the radial stop mechanism of the tandem includes a flat radial-locking surface formed in the connecting portion of the shaft of the tandem, the flat radial-locking surface being formed in a plane extending parallel to the axis of the tandem, and the radial stop mechanism of the tandem further includes an axial stop surface being perpendicular or nearly perpendicular to the flat radial-locking surface, and wherein the connector bracket includes a corresponding flat radial-locking surface configured to engage and contact the flat radial-locking surface of the tandem when the tandem is locked to the connector bracket.

10. The brachytherapy ring applicator according to claim 9, wherein the ring colpostat includes:

a radial stop mechanism provided on the shaft of the ring colpostat, the radial stop mechanism of the ring colpostat being configured to engage a locking portion of the bracket assembly to prevent movement around an axis of the shaft of the ring colpostat when the radial stop mechanism of the ring colpostat is engaged with a connector bracket of the bracket assembly, and an axial stop member provided on a connecting portion of the ring colpostat, the axial stop member being configured to prevent movement in a direction parallel with the axis of the shaft of the ring colpostat when the axial stop member is engaged with the connector bracket of the bracket assembly, wherein the radial stop mechanism of the ring colpostat includes a flat radial-locking surface formed in the connecting portion of the shaft of the ring colpostat, the flat radial-locking surface being formed in a plane extending parallel to the axis of the shaft of the ring colpostat, and the radial stop mechanism of the ring colpostat further includes an axial stop surface being perpendicular or nearly perpendicular to the flat radial-locking surface, and wherein the connector bracket includes a corresponding flat radial-locking surface configured to engage and contact the flat radial-locking surface of the ring colpostat when the ring colpostat is locked to the connector bracket.

11. The brachytherapy ring applicator according to claim 1, wherein the ring colpostat includes a radial stop mechanism provided on the shaft of the ring colpostat, the radial stop mechanism of the ring colpostat being configured to engage a locking portion of the bracket assembly to prevent movement around an axis of the shaft of the ring colpostat when the radial stop mechanism of the ring colpostat is engaged with the connector bracket of the bracket assembly.

12. The brachytherapy ring applicator according to claim 11, wherein the radial stop mechanism of the ring colpostat includes a flat radial-locking surface formed in the connecting portion of the shaft of the ring colpostat, the flat radial-locking surface being formed in a plane extending parallel to the axis of the ring colpostat, and the radial stop mechanism of the ring colpostat further includes an axial stop surface being perpendicular or nearly perpendicular to the flat radial-locking surface, and wherein the connector bracket includes a corresponding flat radial-locking surface configured to engage and contact the flat radial-locking surface of the ring colpostat when the ring colpostat is locked to the connector bracket.

13. The brachytherapy ring applicator according to claim 1, wherein the ring colpostat includes an axial stop member provided on a connecting portion of the ring colpostat, the axial stop member being configured to prevent movement in a direction parallel with the axis of a shaft of the ring colpostat when the axial stop member is engaged with a connector bracket of the bracket assembly.

14. The brachytherapy ring applicator according to claim 1, wherein the shaft of the tandem and the shaft of the ring colpostat are sufficiently rigid such that in the case that the connecting portion of the shaft of the tandem and a connecting portion of the shaft of the ring application is locked to the bracket assembly, the shaft of the tandem and the shaft of the ring colpostat remain substantially parallel and the distal end of the tandem remains in a fixed position relative to the distal end of the ring colpostat while the tandem and the ring colpostat are inserted into a patient.

15. The brachytherapy ring applicator according to claim 1, further comprising a rectal assembly including a rectal paddle, a rectal shaft, and rectal connector, wherein the rectal paddle is configured to engage a posterior vaginal wall of a patient and retract a rectal region from the tandem and colpostat, the rectal paddle extending distally from the rectal shaft and the rectal connector connecting the rectal paddle and the rectal shaft to the shaft of the tandem.

16. The brachytherapy ring applicator according to claim 1, wherein the first threaded locking portion is provided in a first side of the connector bracket, and the bracket assembly further includes a corresponding second threaded locking portion provided in a second side of the connector bracket, the first side of the connector bracket being opposite from the second side of the connector bracket, the second threaded locking portion being configured to receive the separable threaded locking screw and has an axis arranged at an angle offset from perpendicular to a plane in which the shaft of the tandem and the shaft of the ring colpostat extend, such that the second threaded locking portion may alternatively receive the threaded locking screw and contribute a locking force to maintain the connecting portion of shaft of the tandem within the first channel in which the shaft of the tandem is locked.

17. The brachytherapy ring applicator according to claim 1, wherein the connector end of the tandem is configured to be coupled to an afterloading apparatus, and the treatment end includes a treatment portion extending in a direction offset from an axis of the shaft of the tandem by a first angle, and the ring member extends in a direction offset from an axis of the shaft of the ring application by a second angle.

18. A brachytherapy ring applicatory kit comprising:

a plurality of tandems, each of the tandems having a connector on a proximal end of the tandem and a treatment end on a distal end of the tandem, the treatment end being configured to be arranged in proximity to the area to be treated by a radioactive source;

a plurality of ring colpostats, each of the ring colpostats including a ring member on a distal end of the ring colpostat, the ring member being configured to position the treatment end of the tandem; and a bracket assembly configured to be locked to both a shaft of one of said plurality of tandems and to a shaft of one of said ring colpostats such that the distal end of said one of said tandems is firmly maintained in a fixed position relative to the distal end of said one of said ring colpostats, wherein said plurality of tandems, said plurality of ring colpostats, and said bracket assembly are configured such that, when one of said plurality of tandems and one of said plurality of ring colpostats are locked to the bracket assembly, said one of said plurality of tandems, from a location of attachment of the shaft of said one of said plurality of tandems to the bracket assembly to the distal end of said one of said plurality of tandems, and said one of said plurality of ring colpostats, from the location of attachment of the shaft of said one of said plurality of ring colpostat to the bracket assembly to the distal end of said one of said plurality of ring colpostat, are entirely self-supporting, wherein the bracket assembly includes a connector bracket having a first channel, the first channel being an open channel configured to be locked to a connecting portion of the shaft of the one of said plurality of tandems, and wherein the bracket assembly includes a separable threaded locking screw and a corresponding threaded locking portion formed in the connector bracket, the threaded locking portion being configured to receive the separable threaded locking screw, wherein the threaded locking portion has an axis arranged at an angle offset from perpendicular to a plane in which the shaft of the one of said plurality of tandems and the shaft of the one of said plurality of ring colpostat extend, such that the threaded locking screw contributes a locking force to maintain the connecting portion of shaft of the one of said plurality of tandems within the first channel.

19. A brachytherapy method for treating cancer, the method comprising the steps of:

providing a brachytherapy ring applicator, the brachytherapy ring applicator including a tandem having a connector on a proximal end of the tandem and a treatment end on a distal end of the tandem, the treatment end being configured to be arranged in proximity to the area to be treated by a radioactive source;

a ring colpostat including a ring member on a distal end of the ring colpostat, the ring member being configured to position the treatment end of the tandem; and a bracket assembly configured to be locked to both a shaft of the tandem and to a shaft of the ring colpostat such that the distal end of the tandem is firmly maintained in a fixed position relative to the distal end of the ring colpostat, wherein said tandem, said colpostat, and said bracket assembly are configured such that, when the tandem and the ring colpostat are locked to the bracket assembly, the tandem, from a location of attachment of the shaft of the tandem to the bracket assembly to the distal end of the tandem, and the colpostat, from the location of attachment of the shaft of the colpostat to the bracket assembly to the distal end of the colpostat, are entirely self-supporting, wherein the bracket assembly includes a connector bracket having a first channel, the first channel being an open channel configured to be locked to a connecting portion of the shaft of the tandem, and wherein the bracket assembly includes a separable threaded locking screw and a corresponding threaded locking portion formed in the connector bracket, the threaded locking portion being configured to receive the separable threaded locking screw, wherein the threaded locking portion has an axis arranged at an angle offset from perpendicular to a plane in which the shaft of the tandem and the shaft of the ring colpostat extend, such that the threaded locking screw contributes a locking force to maintain the connecting portion of shaft of the tandem within the channel;

locking the shaft of the ring colpostat to the bracket assembly;

inserting the tandem into a patient;

passing the ring member of the ring colpostat around the connector end of the tandem and passing the ring member along the shaft of the tandem to provide the ring member within proximity to the treatment end of the tandem and in proximity to an area to be treated;

passing a portion of the shaft of the tandem through an opening of the open channel of the first channel; and locking the shaft of the tandem to the bracket assembly.

* * * * *